US011559335B2

(12) United States Patent
Jackson et al.

(10) Patent No.: US 11,559,335 B2
(45) Date of Patent: *Jan. 24, 2023

(54) PIVOTAL BONE ANCHOR ASSEMBLY WITH INSERT TOOL DEPLOYMENT

(71) Applicants: Roger P Jackson, Prairie Village, KS (US); James L Surber, Kansas City, KS (US)

(72) Inventors: Roger P Jackson, Prairie Village, KS (US); James L Surber, Kansas City, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 17/581,797

(22) Filed: Jan. 21, 2022

(65) Prior Publication Data

US 2022/0142678 A1    May 12, 2022

Related U.S. Application Data

(63) Continuation of application No. 14/658,721, filed on Mar. 16, 2015, now Pat. No. 11,229,457, which is a continuation of application No. 13/317,387, filed on Oct. 19, 2011, now Pat. No. 8,998,959, which is a continuation-in-part of application No. 12/924,802, (Continued)

(51) Int. Cl.
*A61B 17/70*     (2006.01)
(52) U.S. Cl.
CPC ...... *A61B 17/7037* (2013.01); *A61B 17/7032* (2013.01)
(58) Field of Classification Search
CPC .......................................... A61B 17/7032–7038
See application file for complete search history.

(56) References Cited

U.S. PATENT DOCUMENTS

| 5,669,911 A | 9/1997 | Errico et al. |
| 5,672,176 A | 9/1997 | Biedermann et al. |

(Continued)

FOREIGN PATENT DOCUMENTS

EP    1857064    11/2007

*Primary Examiner* — Lynnsy M Summitt
(74) *Attorney, Agent, or Firm* — Polsinelli PC

(57) ABSTRACT

A pivotal bone anchor assembly includes a bone anchor having a capture portion and an anchor portion opposite the capture portion, and a receiver assembly in a pre-assembled configuration that includes a receiver, a retainer, and a pressure insert. The receiver has a central bore configured to receive the capture portion through a bottom opening, with a lower portion of the central bore including a narrower engagement portion adjacent the bottom opening and a wider expansion portion above the narrower engagement portion. The pre-assembled retainer is configured to widen within the wider expansion portion to receive the capture portion of the bone anchor during its uploading through the bottom opening, then to close around and secure the capture portion while providing for pivotal motion of the bone anchor relative to the receiver. The pre-assembled insert is downwardly deployable with tooling, prior to the installation of a longitudinal connecting member and closure, until an outer surface of the insert comes into forced interference wedged engagement with interference wedging surfaces formed into the central bore so as to inhibit the pressure insert from moving back up within the receiver.

26 Claims, 12 Drawing Sheets

Related U.S. Application Data filed on Oct. 5, 2010, now Pat. No. 8,556,938, said application No. 14/658,721 is a continuation-in-part of application No. 12/802,849, filed on Jun. 15, 2010, now abandoned.

(60) Provisional application No. 61/455,482, filed on Oct. 21, 2010, provisional application No. 61/403,915, filed on Sep. 23, 2010, provisional application No. 61/403,696, filed on Sep. 20, 2010, provisional application No. 61/402,959, filed on Sep. 8, 2010, provisional application No. 61/400,504, filed on Jul. 29, 2010, provisional application No. 61/398,807, filed on Jul. 1, 2010, provisional application No. 61/396,390, filed on May 26, 2010, provisional application No. 61/395,752, filed on May 17, 2010, provisional application No. 61/395,564, filed on May 14, 2010, provisional application No. 61/343,737, filed on May 3, 2010, provisional application No. 61/336,911, filed on Jan. 28, 2010, provisional application No. 61/278,240, filed on Oct. 5, 2009, provisional application No. 61/270,754, filed on Jul. 13, 2009, provisional application No. 61/268,708, filed on Jun. 15, 2009.

(56) References Cited

U.S. PATENT DOCUMENTS

| | | | | |
|---|---|---|---|---|
| 5,690,630 | A | 11/1997 | Errico et al. | |
| 6,010,503 | A | 1/2000 | Richelsoph et al. | |
| 6,063,090 | A | 5/2000 | Schläpfer | |
| 6,090,111 | A | 7/2000 | Nichols | |
| 6,254,602 | B1 | 7/2001 | Justis | |
| 6,355,040 | B1 | 3/2002 | Richelsoph et al. | |
| 6,471,705 | B1 | 10/2002 | Biedermann et al. | |
| 6,565,565 | B1 | 5/2003 | Yuan et al. | |
| 6,626,908 | B2 | 9/2003 | Cooper et al. | |
| 6,740,086 | B2 | 5/2004 | Richelsoph | |
| 6,837,889 | B2 | 1/2005 | Shluzas | |
| 7,066,937 | B2 | 6/2006 | Shluzas | |
| 7,087,057 | B2 | 8/2006 | Konieczynski et al. | |
| 7,144,396 | B2 | 12/2006 | Shluzas | |
| 7,163,539 | B2 | 1/2007 | Abdelgany et al. | |
| 7,264,621 | B2 | 9/2007 | Coates et al. | |
| 7,311,712 | B2 | 12/2007 | Dalton | |
| 7,377,923 | B2 * | 5/2008 | Purcell | A61B 17/7037 606/248 |
| 7,445,627 | B2 | 11/2008 | Hawkes et al. | |
| 7,604,655 | B2 | 10/2009 | Warnick | |
| 7,686,834 | B2 | 3/2010 | Saint Martin | |
| 7,686,835 | B2 | 3/2010 | Warnick | |
| 7,695,497 | B2 | 4/2010 | Cordaro et al. | |
| 7,766,915 | B2 | 8/2010 | Jackson | |
| 7,766,945 | B2 | 8/2010 | Nilsson et al. | |
| 7,776,067 | B2 * | 8/2010 | Jackson | A61B 17/704 606/272 |
| 7,789,896 | B2 | 9/2010 | Jackson | |
| 7,789,900 | B2 * | 9/2010 | Levy | A61B 17/7032 606/267 |
| 7,811,310 | B2 | 10/2010 | Baker et al. | |
| 7,842,073 | B2 | 11/2010 | Richelsoph et al. | |
| 7,901,436 | B2 | 3/2011 | Baccelli | |
| 7,909,830 | B2 | 3/2011 | Frigg et al. | |
| 7,914,536 | B2 | 3/2011 | MacDonald et al. | |
| 7,988,694 | B2 | 8/2011 | Barrus et al. | |
| 8,021,397 | B2 | 9/2011 | Farris et al. | |
| 8,048,112 | B2 | 11/2011 | Suzuki et al. | |
| 8,083,776 | B2 | 12/2011 | Alvarez | |
| 8,221,472 | B2 | 7/2012 | Peterson et al. | |
| 8,382,805 | B2 | 2/2013 | Wang et al. | |
| 8,398,683 | B2 | 3/2013 | Berrevoets et al. | |
| 8,449,578 | B2 | 5/2013 | Keiser et al. | |
| 8,556,938 | B2 | 10/2013 | Jackson et al. | |
| 8,628,558 | B2 | 1/2014 | Harvey et al. | |
| 8,876,869 | B1 | 11/2014 | Schafer et al. | |
| 8,888,827 | B2 | 11/2014 | Harper et al. | |
| 8,951,290 | B2 | 2/2015 | Hammer et al. | |
| 8,986,349 | B1 | 3/2015 | German et al. | |
| 9,259,247 | B2 | 2/2016 | Chandanson et al. | |
| 9,358,047 | B2 | 6/2016 | Mishra et al. | |
| 9,492,204 | B2 | 11/2016 | Biedermann et al. | |
| 9,526,529 | B2 | 12/2016 | Charvet | |
| 9,655,652 | B2 | 5/2017 | Biedermann et al. | |
| 9,707,013 | B2 | 7/2017 | Rezach et al. | |
| 9,763,702 | B2 | 9/2017 | Schlaepfer et al. | |
| 10,039,572 | B2 | 8/2018 | Harris et al. | |
| 10,064,657 | B2 | 9/2018 | Spitler | |
| 10,154,859 | B2 | 12/2018 | Keyer et al. | |
| 10,172,647 | B2 | 1/2019 | Elsbury | |
| 10,188,432 | B2 | 1/2019 | Jackson et al. | |
| 10,463,402 | B2 | 11/2019 | Biester et al. | |
| 10,695,100 | B2 | 6/2020 | May et al. | |
| 10,792,074 | B2 | 10/2020 | Jackson | |
| 2003/0149431 | A1 | 8/2003 | Varieur | |
| 2006/0058788 | A1 | 3/2006 | Hammer et al. | |
| 2006/0161152 | A1 | 7/2006 | Ensign et al. | |
| 2006/0217716 | A1 | 9/2006 | Baker et al. | |
| 2006/0276789 | A1 * | 12/2006 | Jackson | A61B 17/8605 606/301 |
| 2007/0118123 | A1 | 5/2007 | Strausbaugh et al. | |
| 2007/0135817 | A1 * | 6/2007 | Ensign | A61B 17/7007 606/96 |
| 2007/0270813 | A1 | 11/2007 | Garamszegi | |
| 2009/0143827 | A1 * | 6/2009 | Levy | A61B 17/7037 606/301 |
| 2010/0152787 | A1 * | 6/2010 | Walsh | A61B 17/7037 606/305 |
| 2010/0152788 | A1 * | 6/2010 | Warnick | A61B 17/7037 606/308 |
| 2013/0218213 | A1 | 8/2013 | Lemoine | |

\* cited by examiner

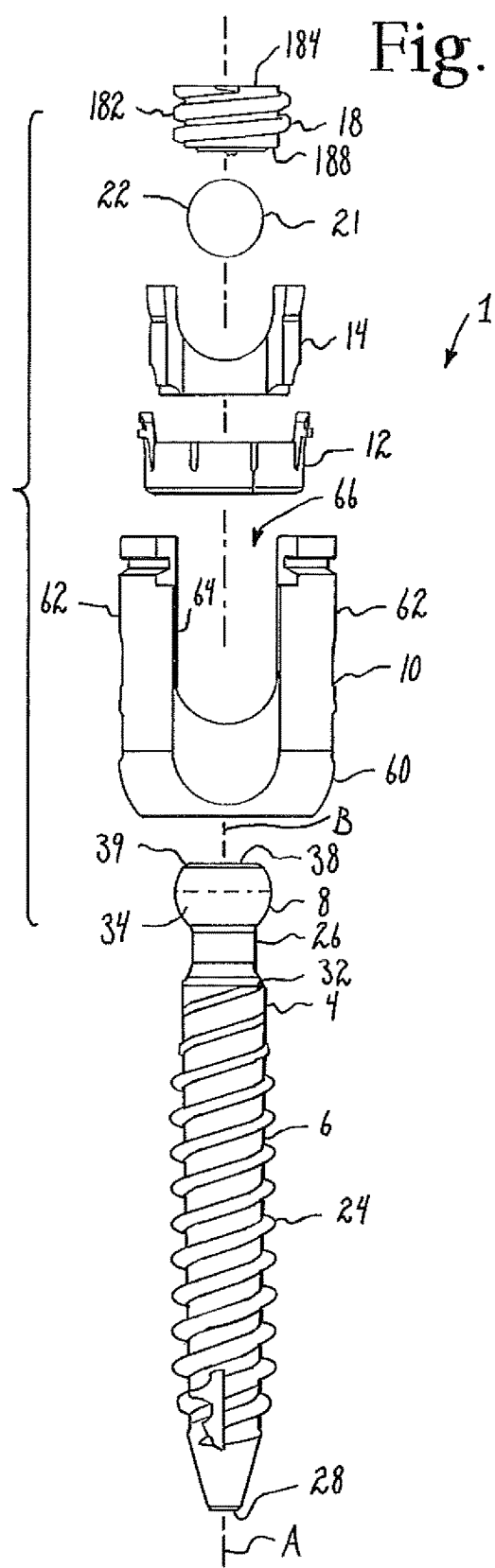
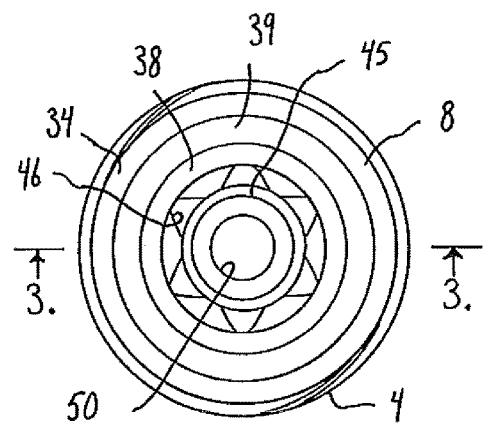
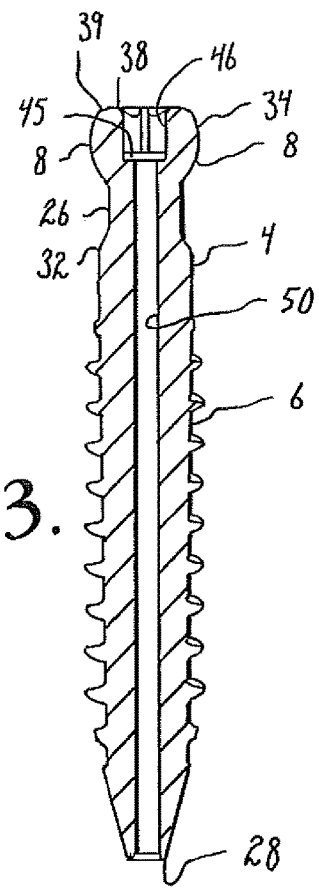

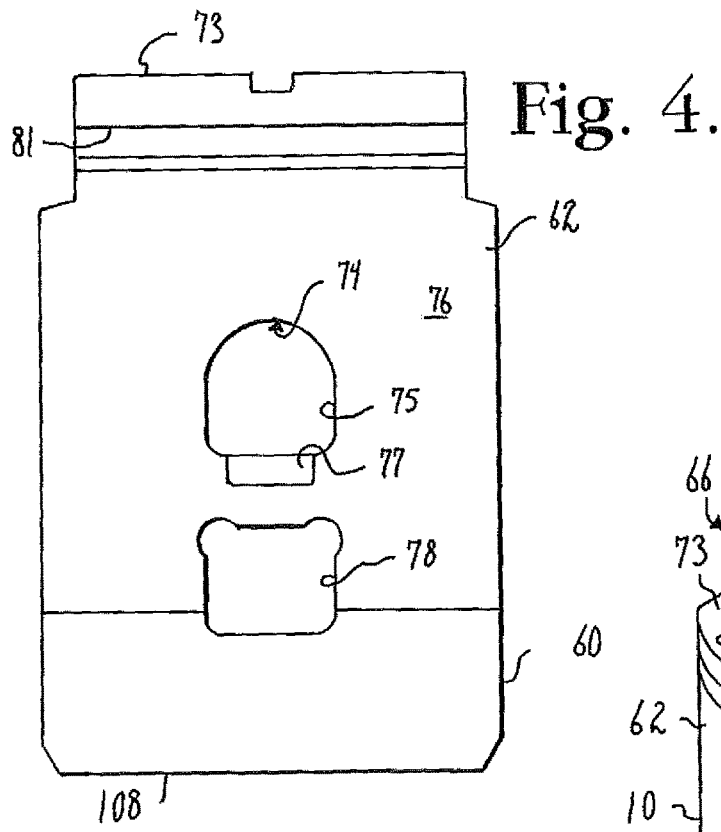
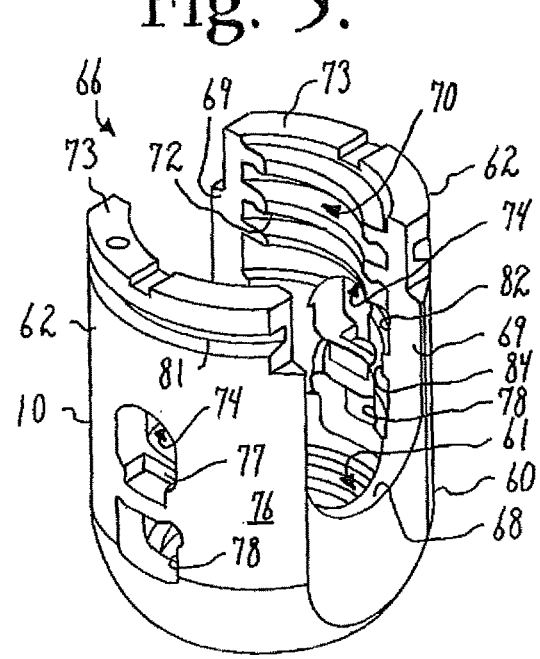
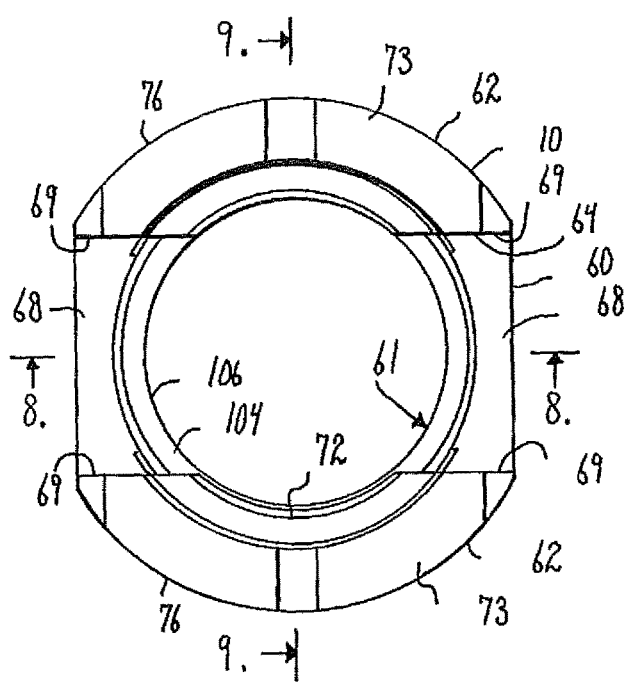

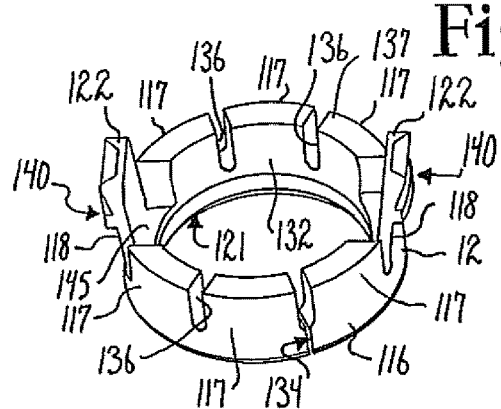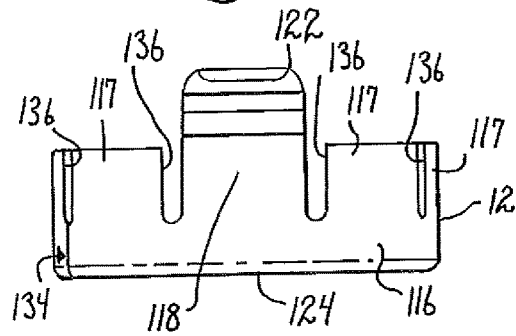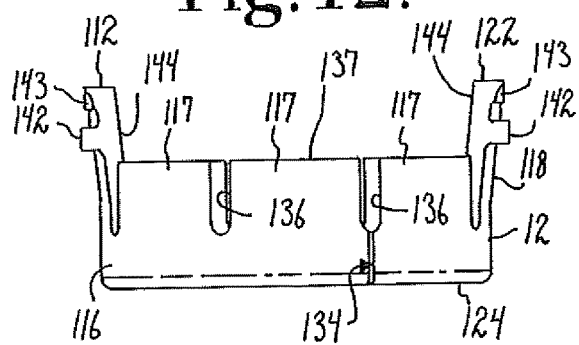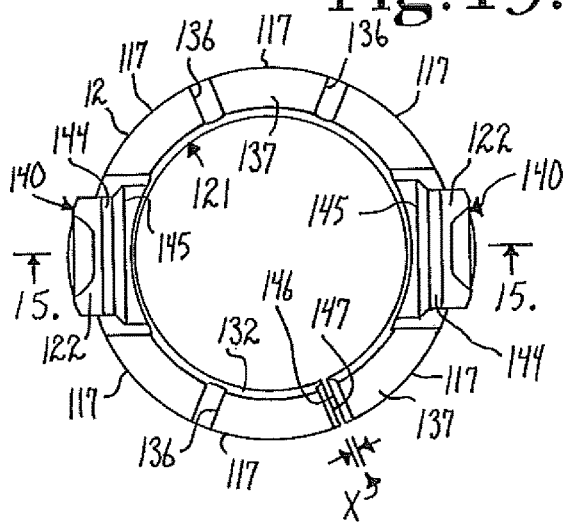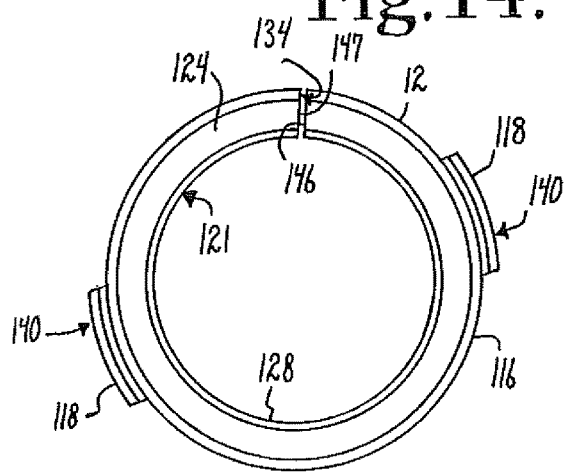

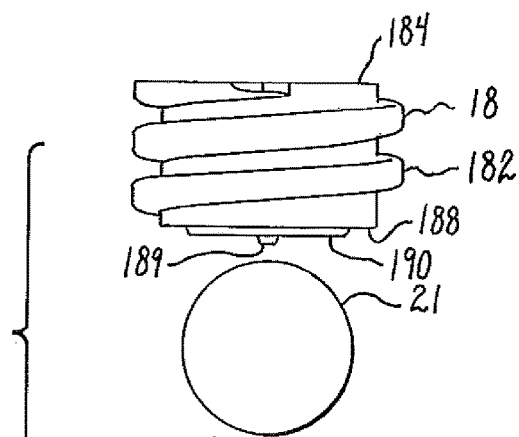
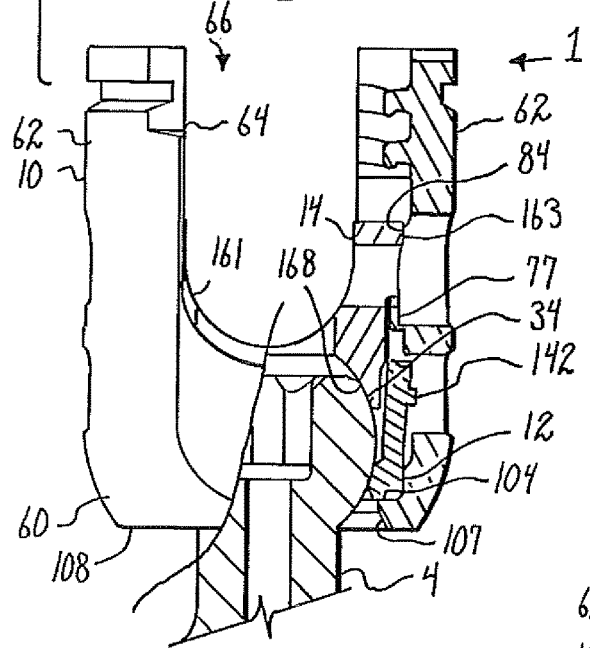
Fig. 36.
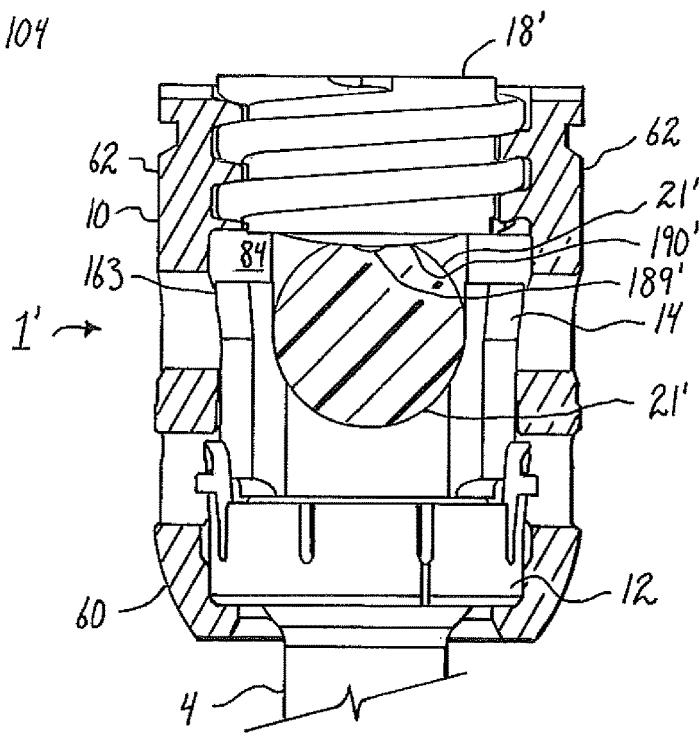
Fig. 37.

PIVOTAL BONE ANCHOR ASSEMBLY WITH INSERT TOOL DEPLOYMENT

CROSS REFERENCE TO RELATED APPLICATIONS

This application is a continuation of U.S. patent application Ser. No. 14/658,721, filed Mar. 16, 2015, which is a continuation of Ser. No. 13/317,387, filed Oct. 19, 2011, now U.S. Pat. No. 8,998,959, which claims the benefit of U.S. Provisional Application No. 61/455,842, filed Oct. 21, 2010, each of which is incorporated by reference in its entirety herein, and for all purposes.

U.S. patent application Ser. No. 13/317,387 is also a continuation-in-part of U.S. patent application Ser. No. 12/924,802, filed Oct. 5, 2010, now U.S. Pat. No. 8,556,938, and which application Ser. No. 12/924,802 claims the benefit of the following U.S. Provisional Patent Applications: U.S. Provisional Application No. 61/278,240, filed Oct. 5, 2009; U.S. Provisional Application No. 61/336,911, filed Jan. 28, 2010; U.S. Provisional Application No. 61/343,737, filed May 3, 2010; U.S. Provisional Application No. 61/395,564, filed May 14, 2010; U.S. Provisional Application No. 61/395,752, filed May 17, 2010; U.S. Provisional Application No. 61/396,390, filed May 26, 2010; U.S. Provisional Application No. 61/398,807, filed Jul. 1, 2010; U.S. Provisional Application No. 61/400,504, filed Jul. 29, 2010; U.S. Provisional Application No. 61/402,959, filed Sep. 8, 2010; U.S. Provisional Application No. 61/403,696, filed Sep. 20, 2010; and U.S. Provisional Application No. 61/403,915, filed Sep. 23, 2010. Each of the above applications is incorporated by reference in its entirety herein, and for all purposes.

U.S. patent application Ser. No. 14/658,721 is also a continuation-in-part of U.S. patent application Ser. No. 12/802,849, filed Jun. 15, 2010, now abandoned, and which application Ser. No. 12/802,849 claims the benefit of the following U.S. Provisional Patent Applications: U.S. Provisional Application No. 61/268,708, filed Jun. 15, 2009; U.S. Provisional Application No. 61/270,754, filed Jul. 13, 2009; U.S. Provisional Application No. 61/336,911, filed Jan. 28, 2010; U.S. Provisional Application No. 61/395,564, filed May 14, 2010; U.S. Provisional Application No. 61/395,752, filed May 17, 2010; and U.S. Provisional Application No. 61/396,390, filed May 26, 2010. Each of the above applications is incorporated by reference in its entirety herein, and for all purposes.

BACKGROUND OF THE INVENTION

The present invention is directed to polyaxial bone screw shanks with heads for use in bone surgery, more specifically to spinal surgery and particularly to such screws with receiver member assemblies including compression or pressure inserts and expansion-only split retainers to snap over, capture and retain the bone screw shank head in the receiver member assembly and later fix the bone screw shank with respect to the receiver assembly.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult. Also, it is often desirable to insert the bone screw shank separate from the receiver or head due to its bulk which can get in the way of what the surgeon needs to do. Such screws that allow for this capability are sometimes referred to as modular polyaxial screws.

With specific reference to modular snap-on or pop-on polyaxial pedicle screw systems having shank receiver assemblies, the prior art has shown and taught the concept of the receiver and certain retainer parts forming an assembly wherein a contractile locking engagement between the parts is created to fix the shank head with respect to the receiver and retainer. The receiver and shank head retainer assemblies in the prior art have included a contractile retainer ring and/or a lower pressure insert with an expansion and contraction collet-type of structure having contractile locking engagement for the shank head due to direct contact between the retainer and/or the collet structure with the receiver resulting in contraction of the retainer ring and/or the collet-type structure of the insert against the shank head.

The prior art for modular polyaxial screw assemblies has also shown and taught that the contact surfaces on the outside of the collect and/or retainer and the inside of the receiver can be tapered, conical, radiused, spherical, curvate, multi-curvate, rounded, as well as other configurations to create a contractile type of locking engagement for the shank head with respect to the receiver.

In addition, the prior art for modular polyaxial screw assemblies has shown and taught that the shank head can both enter and escape from a collet-like structure on the insert or from the retainer when the insert or retainer is in the up position and within the expansion recess or chamber of the receiver. This is the case unless the insert and/or the retainer are blocked from being able to be pushed back up into receiver bore or cavity.

SUMMARY OF THE INVENTION

The present invention differentiates from the prior art by not allowing the receiver to be removed from the shank head once the parts are snapped-on and connected. This is true even if the retainer can go back up into the expansion chamber. This approach or design has been found to be more secure and to provide more resistance to pull-out forces compared to the prior art for modular polyaxial screw designs. Collect-like structures extending downwardly from lower pressure inserts, when used in modular polyaxial screw designs, as shown in the prior art, have been found to be somewhat weak with respect to pull-out forces encountered during some spinal reduction procedures. The present invention is designed to solve these problems.

The present invention also differentiates from all of the prior art by providing a split retainer ring with a collet-like upper portion or super structure, wherein the collet-like structure having inwardly facing panels or fingers does not participate at all in the locking engagement for the shank head with respect to the receiver. In addition, the retainer ring itself for the present invention is uniquely characterized by a base portion providing expansion to receive and capture the shank head and then having only expansion (not contraction) locking engagement between the shank head and the retainer ring base and between the retainer ring base and horizontal and vertical loading surfaces near a bottom opening of the receiver.

The expansion-only retainer ring base in the present invention is positioned entirely below the shank head hemisphere in the receiver and can be a stronger, more substantial structure to resist larger pull out forces on the assembly. The retainer ring base can also be better supported on a generally horizontal loading surface near the lower opening in the bottom of the receiver. This design has been found to be stronger and more secure when compared to that of the prior art which uses some type of contractile locking engagement between the parts, as described above; and, again, once assembled it cannot be disassembled.

Thus, a polyaxial bone screw assembly according to the invention includes a shank having an integral upper portion or integral spherical head and a body for fixation to a bone; a separate receiver defining an upper open channel, a central bore, a lower cavity and a lower opening; a top drop and turn in place lower compression insert; and a friction fit resilient expansion-only split retainer for capturing the shank head in the receiver lower cavity, the shank head being frictionally engaged with, but still movable in a non-floppy manner with respect to the friction fit retainer and the receiver prior to locking of the shank into a desired configuration. The compression insert operatively engages the shank head and is spaced from the retainer by the head that is snapped into the resilient retainer. The shank is finally locked into a fixed position relative to the receiver by frictional engagement between the insert and a lower split ring-like portion of the retainer base, as described previously, due to a downward force placed on the compression insert by a closure top pressing on a rod, or other longitudinal connecting member, captured within the receiver bore and channel. In the illustrated embodiments, retainers and compression inserts are downloaded into the receiver, but uploaded embodiments are also foreseen. The shank head can be positioned into the receiver lower cavity at the lower opening thereof prior to or after insertion of the shank into bone. Some compression inserts include a lock and release feature for independent locking of the polyaxial mechanism os the screw can be used like a fixed monoaxial screw. The shank can be cannulated for minimally invasive surgery applications. The receiver can have crimp tabs, but is devoid of any type of spring tabs or collet-like structures. The lower pressure insert and/or the retainer are both devoid of any type of receiver-retainer contractile locking engagements with respect to the shank head. The retainer can also have upwardly extending spring tabs which are deployed into openings in the receiver cavity so that the retainer and captured shank head are stabilized and retained in the region of the receiver locking chamber once they enter into this lower portion of the receiver cavity. In this way, the shank head and retainer cannot go back up into the receiver cavity.

Again, a pre-assembled receiver, compression insert and friction fit split retainer may be "pushed-on", "snapped-on" or "popped-on" to the shank head prior to or after implantation of the shank into a vertebra. Such a "snapping on" procedure includes the steps of uploading the shank head into the receiver lower opening, the shank head pressing against the base portion of the split retainer ring and expanding the resilient lower open retainer portion out into an expansion portion or chamber of the receiver cavity followed by an elastic return of the retainer back to an original or nominal shape thereof after the hemisphere of the shank head or upper portion passes through the lower ring-like portion of the retainer. The shank head also enters into the friction fit upper portion or super structure of the retainer, the panels of the friction fit portion of the retainer snapping onto the shank head as the retainer returns to a neutral or close to neutral orientation, providing a non-floppy connection between the retainer and the shank head. The friction fit between the shank head and the retainer is temporary and not part of the final locking mechanism. In the illustrated embodiment, when the shank is ultimately locked between the compression insert and the lower portion of the retainer, the friction fit collet-like panels of the retainer are no longer in a friction fit engagement with the shank head and they are not in contact with the receiver. The final fixation occurs as a result of a locking expansion-type of contact between the shank head and the lower portion of the split retainer and an expansion-type of non-tapered locking engagement between the lower portion of the retainer ring and the locking chamber in the lower portion of the receiver cavity. The retainer can expand more in the upper portion or expansion chamber of the receiver cavity to allow the shank head to pass through, but has restricted expansion to retain the shank head when the retainer lower ring portion is against the locking chamber surfaces in the lower portion of the receiver cavity and the shank head is forced down against the retainer ring during final locking. In some embodiments, when the polyaxial mechanism is locked, the insert is wedged against a surface of the receiver resulting in a tapered locking engagement, allowing for adjustment or removal of the rod or other connecting member without loss of a desired angular relationship between the shank and the receiver. This independent locking feature allows the polyaxial screw to function like a fixed monoaxial screw.

It is foreseen that the lower pressure insert could also be configured to be independently locked by a tool or instrument, thereby allowing the pop-on polyaxial screw to be distracted, compressed and/or rotated along and around the rod to provide for improved spinal correction techniques. Such a tool would engage the pop-on receiver from the sides and then engage the insert and wedge or force the insert down into a locked position within the receiver. With the tool still in place and the correction maintained, the rod could then be locked within the receiver channel by a closure top followed by removal of the tool. This process could involve multiple screws all being manipulated simultaneously with multiple tools to achieve the desired correction.

It is noted that once the shank head is captured by the retainer ring and the retainer and head are moved down into the locking chamber region of the receiver cavity, retainer spring tabs are deployed outwardly stabilizing the retainer so that the retainer cannot go back up into the receiver cavity. This spring tab deployment also creates good rotational stability between the retainer and receiver and provides for an additional rotational friction fit between the shank head and the receiver itself since the retainer cannot axially rotate in the receiver.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded front elevational view of a polyaxial bone screw assembly according to the present invention including a shank, a receiver without spring tabs, an open friction fit expansion-only retainer and a top drop and turn in place lower compression insert, further shown with a portion of a longitudinal connecting member in the form of a rod and a closure top.

FIG. 2 is an enlarged top plan view of the shank of FIG. 1.

FIG. 3 is reduced cross-sectional view taken along the line 3-3 of FIG. 2.

FIG. 4 is an enlarged side elevational view of the receiver of FIG. 1.

FIG. 5 is a reduced perspective view of the receiver of FIG. 4.

FIG. 6 is a reduced top plan view of the receiver of FIG. 4.

FIG. 10 is an enlarged perspective view of the retainer of FIG. 1.

FIG. 11 is an enlarged side elevational view of the retainer of FIG. 10.

FIG. 12 is an enlarged front elevational view of the retainer of FIG. 10.

FIG. 13 is an enlarged top plan view of the retainer of FIG. 10.

FIG. 14 is an enlarged bottom plan view of the retainer of FIG. 10.

FIG. 15 is a cross-sectional view taken along the line 15-15 of FIG. 13.

FIG. 36 is a reduced and partial front elevational view with portions broken away, similar to FIG. 34, showing the insert retaining the assembly in a locked position when the closure top and the rod are removed.

FIG. 37 is an enlarged and partial front elevational view with portion broken away, similar to FIG. 36, further showing the assembly with a replacement deformable rod and alternative closure top.

DETAILED DESCRIPTION OF THE INVENTION

Figure 7:
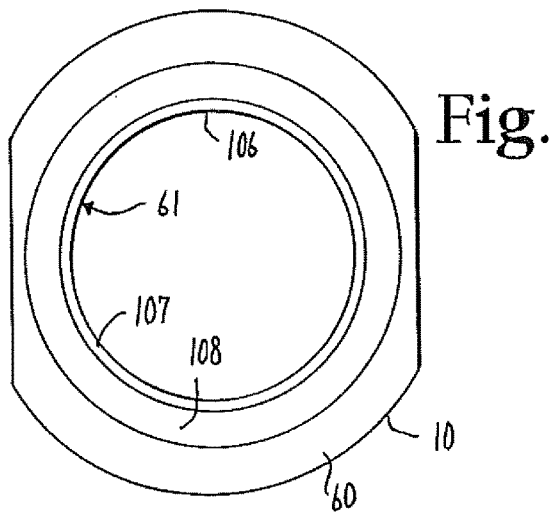
FIG. 7 is a reduced bottom plan view of the receiver of FIG. 4.
Figure 8:
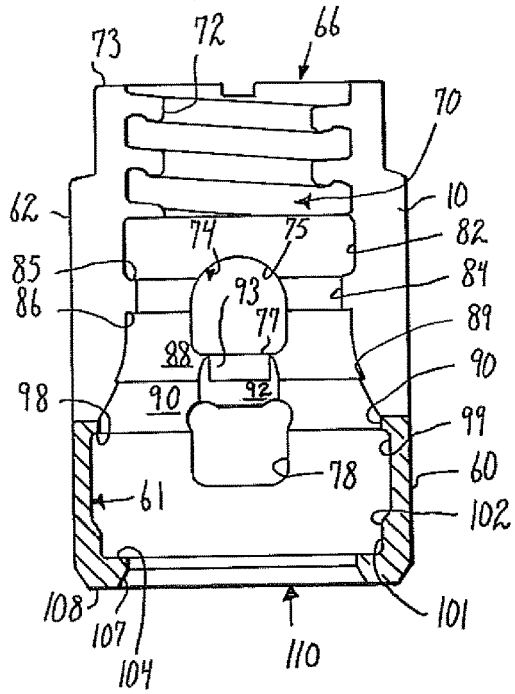
FIG. 8 is a reduced cross-sectional view taken along the line 8-8 of FIG. 6.
Figure 9:
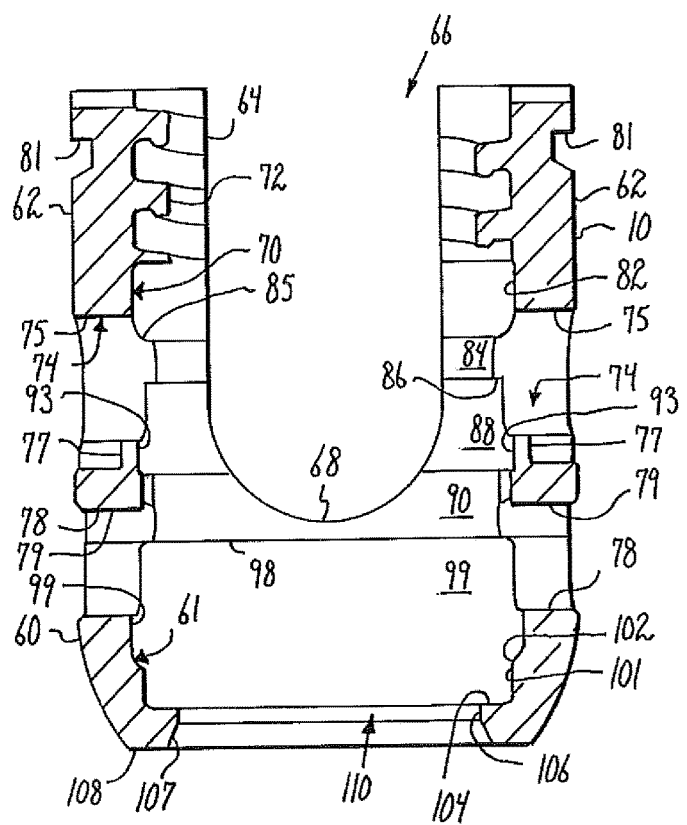
FIG. 9 is an enlarged cross-sectional view taken along the line 9-9 of FIG. 6.
Figure 16:
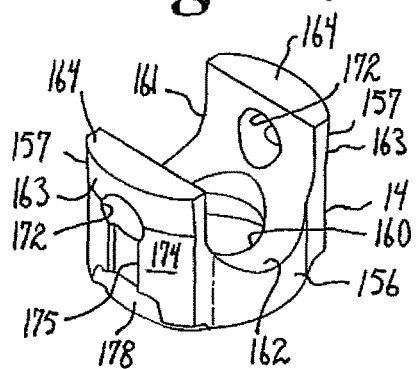
FIG. 16 is an enlarged perspective view of the insert of FIG. 1.
Figure 17:
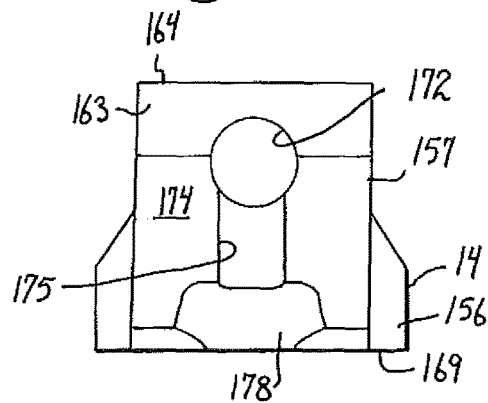
FIG. 17 is an enlarged side elevational view of the insert of FIG. 16.
Figure 18:
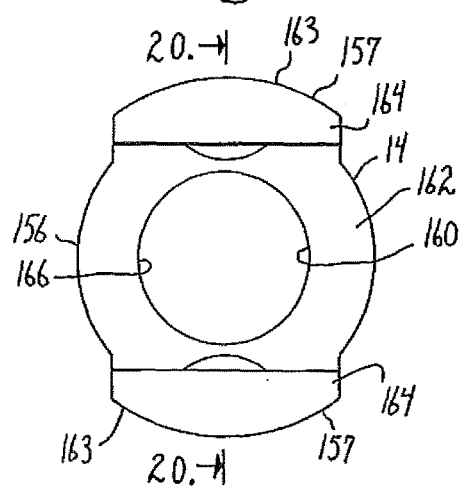
FIG. 18 is an enlarged top plan view of the insert of FIG. 16.
Figure 20:
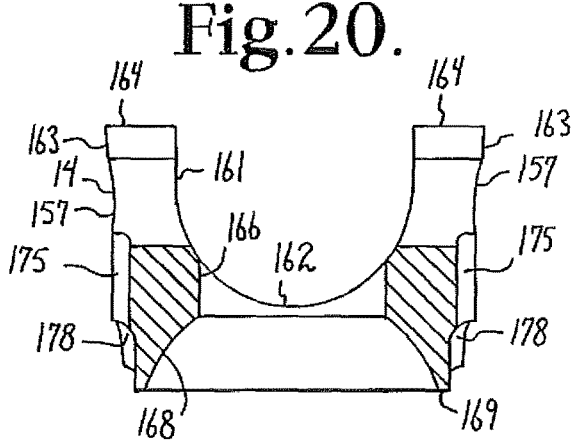
FIG. 20 is a cross-sectional view taken along the line 20-20 of FIG. 18.
Figure 19:
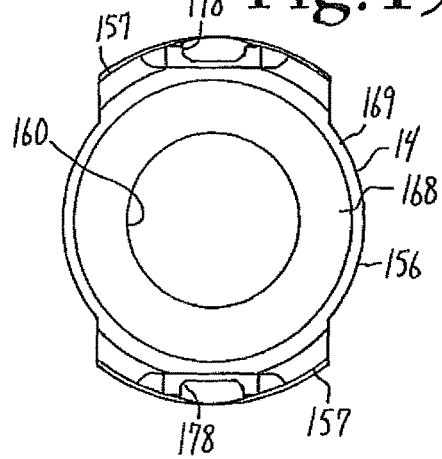
FIG. 19 is an enlarged bottom plan view of the insert of FIG. 16.
Figure 21:
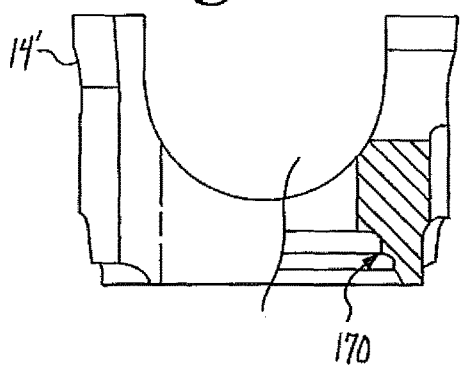
FIG. 21 is an enlarged front elevational view of an alternative insert according to the invention for use in lieu of the insert shown in FIG. 1, with portions broken away to show the detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-39 the reference number 1 generally represents a polyaxial bone screw apparatus or assembly according to the present invention. The assembly 1 includes a shank 4, that further includes a body 6 integral with an upwardly extending upper portion or head structure 8; a receiver 10; a friction fit retainer 12, and a crown-like compression or pressure insert 14. The receiver 10, retainer 12 and compression insert 14 are initially assembled and may be further assembled with the shank 4 either prior or subsequent to implantation of the shank body 6 into a vertebra 17, as will be described in greater detail below. FIGS. 1 and 34-36 further show a closure structure 18 for capturing a longitudinal connecting member, for example, a rod 21 which in turn engages the compression insert 14 that presses against the shank upper portion 8 into fixed frictional contact with the retainer 12, so as to capture, and fix the longitudinal connecting member 21 within the receiver 10 and thus fix the member 21 relative to the vertebra 17. The illustrated rod 21 is hard, stiff, non-elastic and cylindrical, having an outer cylindrical surface 22. It is foreseen that in other embodiments, the rod 21 may be elastic, deformable and/or of different materials and cross-sectional geometries. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The shank 4, best illustrated in FIGS. 1-3, is elongate, with the shank body 6 having a helically wound bone implantable thread 24 (single or dual lead thread form and different thread types) extending from near a neck 26 located adjacent to the upper portion or head 8, to a tip 28 of the body 6 and extending radially outwardly therefrom. During use, the body 6 utilizing the thread 24 for gripping and advancement is implanted into the vertebra 17 leading with the tip 28 and driven down into the vertebra with an installation or driving tool (not shown), so as to be implanted in the vertebra to a location at or near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion or head 8 that provides a connective or capture apparatus disposed at a distance from the upper end 32 and thus at a distance from the vertebra 17 when the body 6 is implanted in such vertebra.

Figure 35:
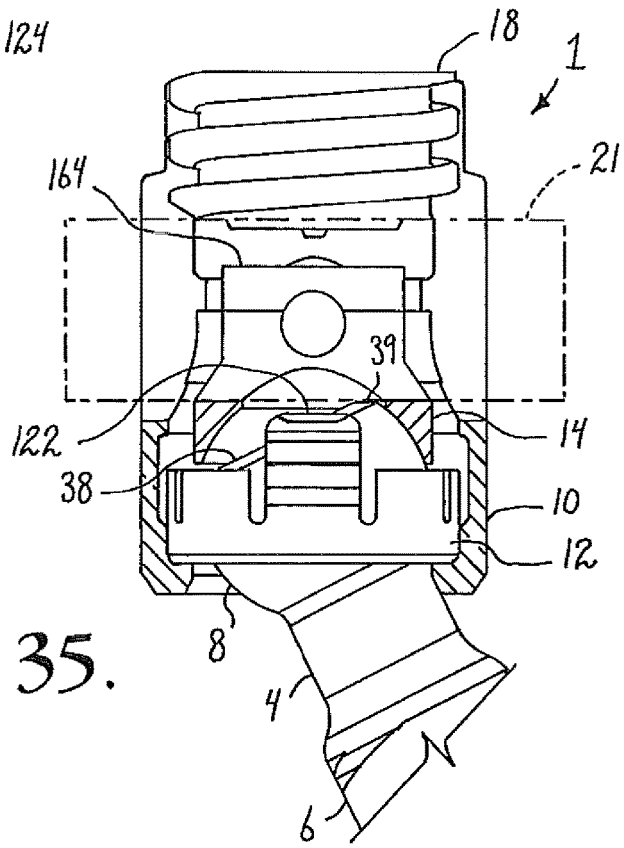
FIG. 35 is an enlarged and partial side elevational view with portions broken away of the entire assembly of FIG. 1, shown locked into position with the shank disposed at an angle with respect to the receiver, the rod being shown in phantom.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 that in some embodiments terminates at a substantially planar top or rim surface 38. In the illustrated embodiment, a frusto-conical surface 39 extends from the spherical surface 34 to the top surface 38, providing additional clearance during shank angulation as best shown in FIG. 35. The spherical surface 34 has an outer radius configured for temporary frictional, non-floppy, sliding cooperation with panels of the retainer 12 having concave or flat surfaces, as well as ultimate frictional engagement with the insert 14 at an inner partially spherical surface thereof, as will be discussed more fully in the paragraphs below. The top surface 38 is substantially perpendicular to the axis A. The spherical surface 34 shown in the present embodiment is substantially smooth, but in some embodiments may include a roughening or other surface treatment and is sized and shaped for cooperation and ultimate frictional engagement with the compression insert 14 as well as ultimate frictional engagement with a lower ring-like portion of the retainer 12. The shank spherical surface 34 is locked into place exclusively by the insert 14 and the retainer 12 lower portion and not by inner surfaces defining the receiver cavity.

A counter sunk substantially planar base or stepped seating surface 45 partially defines an internal drive feature or imprint 46. The illustrated internal drive feature 46 is an aperture formed in the top surface 38 and has a star shape designed to receive a tool (not shown) of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or a multi-lobular or hex-shaped aperture. The seat or base surfaces 45 of the drive feature 46 are disposed substantially perpendicular to the axis A with the drive feature 46 otherwise being coaxial with the axis A. As illustrated in FIGS. 2 and 3, the drive seat 45 may include beveled or stepped surfaces that may further enhance gripping with the driving tool. In operation, a driving tool (not shown) is received in the internal drive feature 46, being seated at the base 45 and engaging the faces of the drive feature 46 for both driving and rotating the shank body 6 into the vertebra 17, either before the shank 4 is attached to the receiver 10 or after the shank 4 is attached to the receiver 10, with the shank body 6 being driven into the vertebra 17 with the driving tool extending into the receiver 10.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper opening communicating with the external drive 46 at the driving seat 45. The bore 50 is coaxial with the threaded body 6 and the upper portion 8. The bore 50 provides a passage through the shank 4 interior for a length of wire (not shown) inserted into the vertebra 17 prior to the insertion of the shank body 6, the wire providing a guide for insertion of the shank body 6 into the vertebra 17. It is foreseen that the shank could be solid and made of different materials, including metal and non-metals.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-9, the receiver 10 has a generally U-shaped appearance with partially discontinuous and partially cylindrical inner and outer profiles. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 17, the axis B is typically disposed at an angle with respect to the axis A, as shown, for example, in FIG. 35.

The receiver 10 includes a substantially cylindrical base 60 defining a bore or inner cavity, generally 61, the base 60 being integral with a pair of opposed upstanding arms 62 forming a cradle and defining a channel 64 between the arms 62 with an upper opening, generally 66, and a U-shaped lower channel portion or seat 68, the channel 64 having a width for operably snugly receiving the rod 21 or portion of another longitudinal connector between the arms 62, the channel 64 communicating with the base cavity 61. Inner opposed substantially planar arm surfaces 69 partially define the channel 64 directly above the seat 68 and are located on either side of each arm interior surface generally 70, that includes various inner cylindrical profiles, an upper one of which is a partial helically wound guide and advancement structure 72 located adjacent top surfaces 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms 62 could have break-off extensions.

An opposed pair of key-hole like tool receiving and engaging grooves or apertures, generally 74, each having an upper arched through bore 75, are formed on outer surfaces 76 of the arms 62. Each through bore 75 extends between the outer surface 76 and the inner surface 70 and is located above a rectangular shaped shallow recessed arm portion or crimp wall 77 that defines the portion of the aperture 74 that does not extend completely through the respective arm 62. The thin walled portion 77 is pressed or crimped into the insert 14 to prohibit rotation and misalignment of the insert 14 with respect to the receiver 10 as will be described in greater detail below. In other embodiments of the invention, other surfaces forming the groove or aperture 74 may be inwardly crimped. The receiver 10 is an integral structure and devoid of any spring tabs or collet-like structures. Preferably the insert and/or receiver are configured with structure for blocking rotation of the insert with respect to the receiver, such as crimp tabs 77, but allowing some up and down movement of the insert with respect to the receiver during the assembly and implant procedure. Two additional rectangular shaped through bores 78 are also formed in the arms 62 and located directly below the apertures 74. It is foreseen that the opening 78 could assume almost any shape. The through bores 78 are sized and shaped for receiving portions of the retainer 12 during top loading of the retainer 12 into the receiver 10 as will be described more fully below and as shown, for example, in FIG. 22. An upper surface 79 defining each bore 78 functions as an upper stop for a portion of the retainer 12, during shipping and during assembly, as shown, for example, in FIG. 28, and as will be described in greater detail below. Also formed in each outer arm surface 76 near the top surface 73 is an undercut tool receiving and engaging groove 81. Some or all of the apertures 74 and 78 and the groove 81 may be used for holding the receiver 10 during assembly with the insert 14, the retainer 12 and the shank 4; during the implantation of the shank body 6 into a vertebra when the shank is preassembled with the receiver 10; during assembly of the bone anchor assembly 1 with the rod 21 and the closure structure 18; and during lock and release adjustment of the insert 14 with respect to the receiver 10, either into or out of frictional engagement with the inner surfaces of the receiver 10 as will be described in greater detail below. It is foreseen that tool receiving grooves or apertures may be configured in a variety of shapes and sizes and be disposed at other locations on the receiver arms 62.

Returning to the interior surface 70 of the receiver arms 62, located below the guide and advancement structure 72 is a discontinuous cylindrical surface 82 partially defining a run-out feature for the guide and advancement structure 72. The cylindrical surface 82 has a diameter equal to or slightly greater than a greater diameter of the guide and advancement structure 72. Moving downwardly, in a direction toward the base 60, following the cylindrical surface 82 of each arm is a cylindrical or tapered surface 84 partially defined by a run-out seat or surface 85 that extends inwardly toward the axis B and runs perpendicular or somewhat obliquely towards the axis B. The surface 84 has a diameter smaller than the diameter of the surface 82. The surface 84 is sized and shaped to initially closely receive a lower portion of the insert 14 and later frictionally engage a tapered or frusto-conical upper portion of the insert 14, providing a lock and release function that will be described in greater detail below. A discontinuous annular surface 86 is located below and adjacent to the surface 84. The surface 86 is substantially perpendicular to the axis B, but could also be somewhat oblique. Another discontinuous cylindrical surface 88 is located below and adjacent to the surface 86. The surface 88 has a diameter slightly larger than the diameter of the surface 84. A discontinuous annular surface or narrow ledge 89 is located below the surface 88 and is substantially perpendicular to the axis B. A partially discontinuous cylindrical surface 90 is located on each arm below and adjacent to the surface 89. The surface 90 also defines an upper cylindrical surface of the base cavity 61. The surface 90 has a diameter slightly smaller than the diameter of the surface 88 but larger than the diameter of the surface 84. It is noted that in some embodiments of the invention, the surfaces 88 and 90 are combined and form a single smooth cylindrical surface.

The through bores 75 each extend through the arms at the surfaces 82, 84 and 88. The crimping wall 77 is located in an inner recessed surface area 92 that is formed in both the surfaces 88 and 90. In the illustrated embodiment, the crimping wall 77 has an inner surface 93 that is primarily located at the portion of the area 92 that is formed in the cylindrical surface 88. Each through bore 78 is located directly below the area 92. It is foreseen that the crimp wall 77 could be in the form of a deformable crimp tab.

Figure 23:
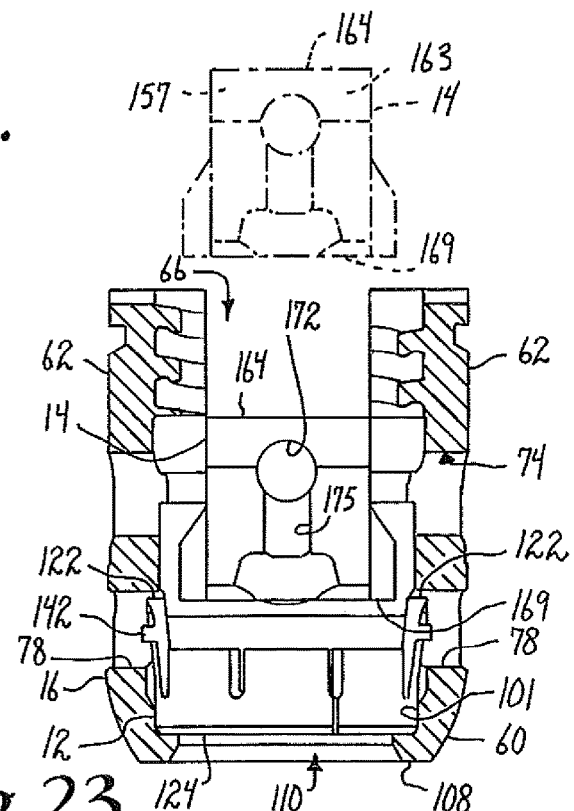
FIG. 23 is a front elevational view of the retainer and receiver with portions broken away, similar to that shown in FIG. 24, further showing the retainer seated within the receiver and also showing the insert of FIG. 1 in side elevation (in phantom) above the receiver and then being downloaded into the receiver to a partially inserted stage of assembly.

An annular surface 98 partially defining the base cavity 61 is located below and adjacent to the cylindrical surface 90. The surface 98 is disposed substantially perpendicular to the axis B, but could be oblique. Another cylindrical surface 99 is located below and adjacent to the surface 98. The cylindrical surface 99 is oriented substantially parallel to the axis B and is sized and shaped to receive an expanded portion of retainer 12. The surfaces 98 and 99 define a circumferential recess that is sized and shaped to receive the retainer 12 as it expands around the shank upper portion 8 as the shank 8 moves upwardly toward the channel 64 during assembly. It is foreseen that the recess could be tapered or conical in configuration. A cylindrical surface 101 located below the cylindrical surface 99 is sized and shaped to closely receive and surround a lower portion of the retainer 12 when the retainer is in a substantially neutral position as shown in FIG. 23, for example. Thus, the cylindrical surface 101 has a diameter smaller than the diameter of the cylindrical surface 99 that defines the expansion area or expansion chamber for the retainer 12. The surface 101 is joined or connected to the surface 99 by one or more beveled, curved or conical surfaces 102. The surfaces 102 allow for sliding and neutral or nominal positioning of the retainer 12 into the space defined by the surface 101 and ultimate seating of the retainer 12 on a lower substantially horizontal annular surface 104 located below and adjacent to the cylindrical surface 101.

Located below and adjacent to the annular seating surface 104 is another substantially cylindrical surface 106 that communicates with a beveled or flared bottom opening surface 107, the surface 107 communicating with an exterior base surface 108 of the base 60, defining a lower opening, generally 110, into the base cavity 61 of the receiver 10.

Figure 34:
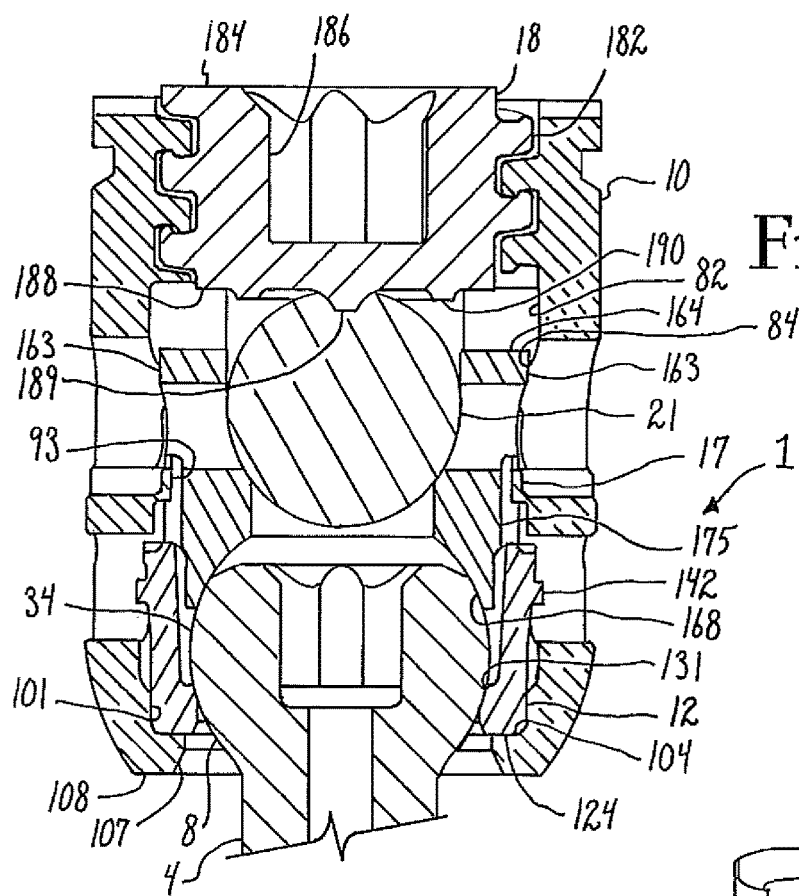
FIG. 34 is an enlarged and partial front elevational view with portions broken away of the entire assembly of FIG. 1, the assembly shown in a locked position with the insert wedged against surfaces of the receiver.

With particular reference to FIGS. 1 and 10-15, the lower open or split friction fit retainer 12, that operates to capture the shank upper portion 8 within the receiver 10, has a central axis that is operationally the same as the axis B associated with the receiver 10 when the shank upper portion 8 and the retainer 12 are installed within the receiver 10. The retainer 12 includes a substantially cylindrical discontinuous lower body 116, a plurality of flex fingers or panels, 117 extending upwardly from the body 116 and a pair of opposed spring arms or tabs 118, also extending upwardly from the body 116. The retainer ring 12 is made from a resilient material, such as a stainless steel or titanium alloy, so that the retainer 12 body 116 may be expanded and the panels and tabs (117 and 118) of the retainer may be manipulated during various steps of assembly as will be described in greater detail below. The retainer 12 has a central channel or hollow through bore, generally 121, that passes entirely through the retainer 12 from tab 118 top surfaces 122 to a bottom surface 124 of the retainer body 116. Surfaces that define the channel or bore 121 include an inner lower frusto-conical surface 128 adjacent to the retainer body bottom surface 124, a substantially cylindrical surface 130 adjacent the frusto-conical surface 128, a narrow frusto-conical or beveled surface 131 adjacent the cylindrical surface 130 and a partially continuous partially discontinuous substantially spherical surface 132 adjacent the surface 131, the surface 132 being substantially continuous near the cylindrical surface 130 with the exception of the opposed spring tabs 118 and a through slot or slit, generally 134. It is foreseen that the surface 131 could also be cylindrical. The surface 132 is in a plurality of segments or pieces at the flex fingers or panels 117 wherein a plurality of substantially evenly spaced slots 136 running outwardly and upwardly through an upper surface 137 separate the surface 132 into the individual flex fingers or panels 117. In the illustrated embodiment, the slots 136 and the through slit 134 form the six substantially uniform flex fingers or panels 117 as well as partially define the two spring tabs 118, each panel having the inner spherical surface 132. It is foreseen that more or fewer flex fingers, tabs or panels may be made by the forming of more or fewer slots 136 and that the surface 132 could be planar or tapered. The discontinuous spherical surface 132 is sized and shaped to closely fit about and snap onto the shank surface 34 during assembly as will be described in greater detail below. Preferably the surface 132 has a radius the same, slightly smaller or slightly larger than the radius of the spherical shank surface 34. The surface 132 could be bent or deformed inwardly or outwardly to better cooperate with the shank head. In operation, the discontinuous surface 132 advantageously frictionally engages the bone screw shank upper portion or head 8, allowing for un-locked but non-floppy placement of the angle of the shank 4 with respect to the receiver 10 during surgery prior to locking of the shank 4 with respect to the receiver 10 near the end of the procedure. At the time of locking engagement, as shown in FIG. 34, for example, downward and outward force placed on the retainer 12 by the shank upper portion 8 expands the retainer body 116 at the slit 134 and the individual flex fingers or panels 117 no longer frictionally grip the spherical head surface 34 of the upper portion 8. To aid in bending flexibility and resiliency, certain flex fingers 117 may have sloping outer surfaces or other geometry to gain the level of resiliency desired for expansion and gripping of the fingers 117 about the shank upper portion 8. The spherical surfaces 132 may include a surface treatment or roughening to provide a desired friction fit. Again, it is noted that the surfaces 132 need not be spherical and may be planar or faceted or include other surface geometries that resiliently grip the shank upper portion or head 8. Again, in some embodiments, the flexible panels or tabs 117 may be bent or deformed to further enhance frictional engagement. It is noted that the fingers 117 that are directed generally upwardly toward the receiver channel 64 advantageously sufficiently snap about and then grip the shank surface 34 to an extent to provide the friction fit desired for non-floppy placement of the shank body 6 at a desired angle with respect to the receiver 10 during manipulation of the bone screws 1 and the rod 21 or other longitudinal connecting member during surgery. However, as compared to bone screw inserts such as collets known in the art that include downwardly directed portions or panels that are ultimately wedged between a receiver surface and a shank surface upon final locking of the shank to the receiver, the thin upwardly directed fingers or panels 117 that extend away from the shank locking surface that are not as strong as the retainer body 116 or the insert 114, do not participate or cooperate with the final locking of the insert 114 to the shank upper portion 8, the shank upper portion 8 to the retainer 12, and the retainer 12 to the receiver inner and substantially planar surfaces 101 and 104. For such purpose, the more substantial retainer body 116 having only the very narrow slit 134, used for expansion purposes only, is the component that locks the shank upper portion 8 between the receiver 10, the insert 114 and the rod 21 or other longitudinal connecting member. In addition, the surface 131 can be cylindrical and provide a sharp edge for the shank head to lock against.

The retainer body 116, the flex fingers 117 and a portion of each of the spring tabs 118 have an outer substantially cylindrical profile, sized and shaped to closely and slidingly fit within the receiver cavity 61 with the exception of outward extensions or wings, generally 140, of the spring tabs 118 that are located adjacent to the upper surfaces 122, each wing extending outwardly away from the respective tab body 118 and having a projected outward surface 142 spaced from each top surface 122 that is sized and shaped to closely cooperate and frictionally engage upper surfaces 79 defining the through bores 78. Outer surfaces 143 located directly beneath each upper surface 122 and above the surfaces 142 are sized and shaped to cooperate with and frictionally engage the cylindrical surface 90 during assembly and shipping as shown, for example, in FIG. 26. The tab wings 140 may include more or fewer projections or notches as needed for tooling to resiliently hold the retainer in an upper portion of the cavity 61 when desired, but readily release the retainer 12 into a lower portion of the receiver cavity 61 once the retainer flex tabs 117 engage the shank head 8. The illustrated spring tabs 118 each includes one or more planar or curved inner surfaces 144 running from the top surface 122 to a tab base surface or seat 145 located adjacent and lateral to the surface 131. The surfaces 144 extend both outwardly and upward from the base surface 145. It is foreseen that in other embodiments of the invention, fewer or greater number of planar or other surfaces with other geometries may extend between the top surface 122 and the inner surfaces defining the body 116 of the retainer 12. Again, the surface 131 can be parallel with the surface 130 and provide a sharp locking edge for the shank head to engage.

The through slit 134 of the resilient retainer 12 is defined by first and second end surfaces, 146 and 147 disposed in spaced relation to one another (they may also be touching) when the retainer is in a neutral state. Both end surfaces 146 and 147 are disposed substantially perpendicular to the bottom surface 124. A width X between the surfaces 146 and 147 is very narrow (slit may be made by EDM process) to provide stability to the retainer 12 during operation. Because the retainer 12 is top loadable in a neutral state and the retainer 12 does not need to be compressed to fit within the receiver cavity 61, the width X may be much smaller than might be required for a bottom loaded compressible retainer ring. The gap X functions only in expansion to allow the retainer 12 to expand about the shank upper portion 8. This results in a stronger retainer that provides more surface contact with the shank upper portion 8 upon locking, resulting in a sturdier connection with less likelihood of failure than a retainer ring having a greater gap. Furthermore, because the retainer 12 body 116 is only expanded and never compressed inwardly, the retainer 12 does not undergo the mechanical stress that typically is placed on spring ring type retainers known in the prior art that are both compressed inwardly and expanded outwardly during assembly.

It is foreseen that in some embodiments of the invention, the retainer 12 inner surfaces may include a roughening or additional material to increase the friction fit against the shank upper portion 8 prior to lock down by the rod 21 or other longitudinal connecting member. Also, the embodiment shown in FIGS. 10-15 illustrates the surfaces 146 and 147 as substantially parallel, however, it is foreseen that it may be desirable to orient the surfaces obliquely or at a slight angle.

With particular reference to FIGS. 1 and 16-21, the lock and release crown compression insert 14 is illustrated that is sized and shaped to be received by and down-loaded into the receiver 10 at the upper opening 66. The compression insert 14 has an operational central axis that is the same as the central axis B of the receiver 10. In operation, the insert advantageously frictionally engages the bone screw shank upper portion 8. Furthermore, as will be described more fully below, an insert 14 that has locked the shank 4 in a desired angular position with respect to the receiver 10, by, for example, compression from the rod 21 and closure top 18, is also wedged into engagement with the receiver 10 at the inner surface 84 and thus retains the shank 6 in a locked position even if the rod 21 and closure top 18 are removed as shown in FIG. 36. Such locked position may also be released by the surgeon if desired. The insert 14 is thus preferably made from a solid resilient material, such as a stainless steel or titanium alloy, so that portions of the insert may be pinched and un-wedged from the receiver 10 with a release tool (not shown).

The lock-and-release compression insert 14 includes a substantially cylindrical body 156 integral with a pair of upstanding arms 157. A bore, generally 160, is disposed primarily within and through the body 156 and communicates with a generally U-shaped through channel 161 that is defined by the upstanding arms 157. The channel 161 has a lower seat 162 sized and shaped to closely, snugly engage the rod 21. It is foreseen that an alternative embodiment may be configured to include planar holding surfaces that closely hold a square or rectangular bar as well as hold a cylindrical rod-shaped, cord, or sleeved cord longitudinal connecting member. The arms 157 disposed on either side of the channel 141 extend upwardly from the body 156. The arms 157 are sized and configured for ultimate placement beneath the cylindrical run-out surface 82 located below the receiver guide and advancement structure 72. It is foreseen that in some embodiments of the invention, for example, when the insert is non-locking as the insert 14" shown in FIGS. 38 and 39, the arms may be extended and the closure top configured such that the arms and, more specifically, the surfaces 164 ultimately directly engage the closure top 18 for locking of the polyaxial mechanism, for example, when the rod 21 is made from a deformable material. In such embodiments, the insert 14 would include a rotation blocking structure or feature that abuts against cooperating structure located on an inner wall of the receiver 10, preventing rotation of the insert with respect to the receiver when the closure top is rotated into engagement with the insert. In the present embodiment, the arms 157 include outer upper flared or frusto-conical surfaces 163 and top surfaces 164 that are ultimately positioned in spaced relation with the closure top 18, so that the closure top 18 frictionally engages the rod 21 only, pressing the rod 21 downwardly against the seating surface 162, the insert 14 in turn pressing against the shank 4 upper portion 8 that presses against the retainer 12 to lock the polyaxial mechanism of the bone screw assembly 1 at a desired angle. As will be discussed in greater detail below, frictional engagement between the insert 14 and the receiver 10, more particularly, the wedging of the tapered surfaces 163 into the cylindrical surfaces 84, provides independent locking of the polyaxial mechanism of the assembly 1, maintaining the upper shank portion 8 in locked engagement by and between the retainer 12 and the insert 14 even if the closure top 18 and/or rod 21 are thereafter removed from the receiver 10.

The bore, generally 160, is substantially defined at the body 156 by an inner cylindrical surface 166 that communicates with the seat 162 and a lower concave substantially spherical surface 168 having a radius the same or substantially similar to a radius of the surface 34 of the shank upper portion 8. The surface 168 terminates at an annular and substantially planar base surface 169 of the body 156. In some embodiments of the invention, located between the cylindrical surface 166 and the spherical surface 168 or located along the spherical surface 168 is a shank gripping surface portion, generally 170, illustrated in FIG. 21 on an alternative insert 14' that is otherwise identical to the insert 14. The gripping surface portion 170 includes one or more stepped surfaces or ridges sized and shaped to grip and penetrate into the shank head 8 when the insert 14' is locked against the head surface 34. It is foreseen that the stepped surface portion 170 may include greater or fewer number of stepped surfaces. It is foreseen that the shank gripping surface portion 170 and also the spherical surface 168 may additionally or alternatively include a roughened or textured surface or surface finish, or may be scored, knurled, or the like, for enhancing frictional engagement with the shank upper portion 8.

The compression insert 14 through bore 160 is sized and shaped to receive the driving tool (not shown) therethrough that engages the shank drive feature 46 when the shank body 6 is driven into bone with the receiver 10 attached. Also, the bore 160 receives a manipulation tool (not shown) used for releasing the insert 14 from a locked position with the receiver, the tool pressing down on the shank and also gripping the insert 14 at through bores 172 located in the arms 157 or with other tool engaging features. A manipulation tool for un-wedging and releasing the insert 14 from the receiver 10 may also access the bores 172 from the receiver through bores 75 in the receiver. Thereby, tools can be configured to release the insert 14 from the inside and outside of the receiver 10.

The illustrated insert 14 further includes other features for manipulating and holding the insert 14 within the receiver 10. Each insert arm 157 includes an outer surface 174 having a substantially vertical groove 175 formed thereon, the groove 175 located below the through bore 172. The grooves 175 cooperate with the receiver crimp wall 77 to aid in alignment of the insert channel 161 with the receiver channel 64. Located beneath each groove 175 is a recessed area or portion 178 sized and shaped to receive and allow clearance for the upper surface 122 of the retainer wings 140, as shown, for example, in FIG. 26, during assembly and shipping of the pre-assembled receiver 10, retainer 12 and insert 14.

The insert body 156 has an outer diameter slightly smaller than a diameter between crests of the guide and advancement structure 72 of the receiver 10, allowing for top loading of the compression insert 14 into the receiver opening 66, with the arms 157 of the insert 14 being located between the receiver arms 62 during insertion of the insert 14 into the receiver 10. Once the arms 157 of the insert 14 are generally located beneath the guide and advancement structure 72, the insert 14 is rotated into place about the receiver axis B until the top surfaces 164 are located directly below the guide and advancement structure 72 as will be described in greater detail below.

Figure 38:
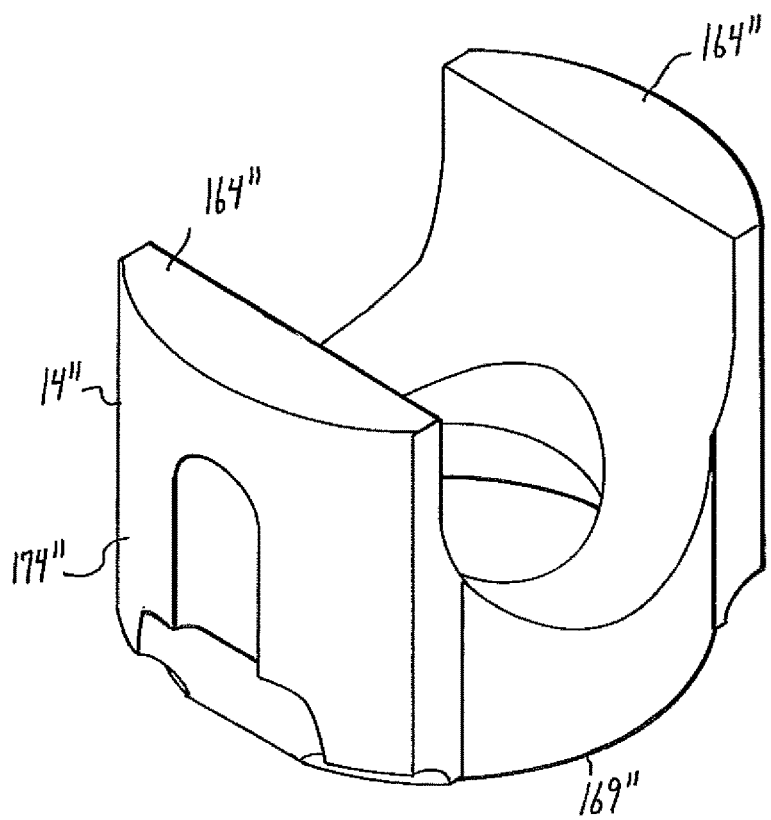
FIG. 38 is an enlarged perspective view of an alternative non-locking insert according to the invention.
Figure 39:
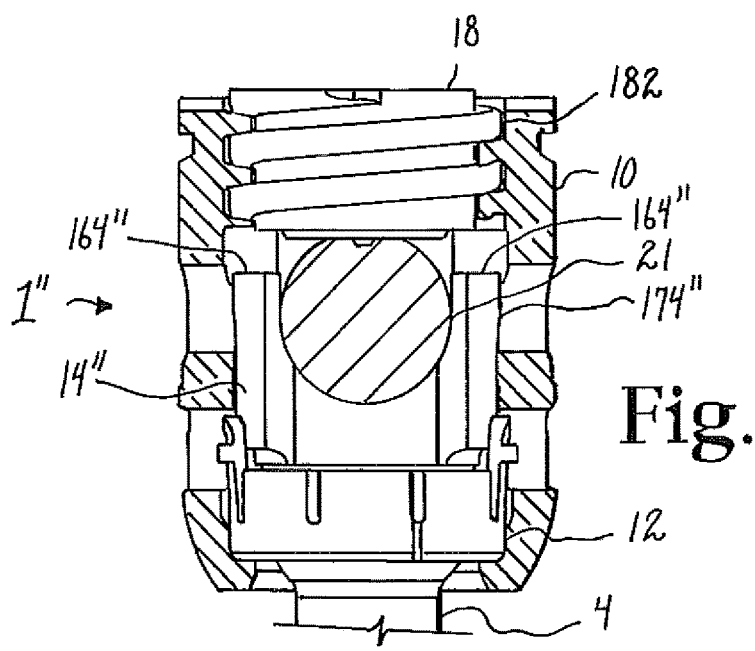
FIG. 39 is an enlarged and partial front elevational view of the assembly of FIG. 1 shown in a fully assembled locked position with the non-locking insert of FIG. 38 in lieu of the locking insert shown in FIG. 1, with portions broken away to show the detail thereof.

With reference to FIGS. 38 and 39, an alternative non-locking insert 14" is identical or substantially similar to the insert 14 with the exception of outer arm surfaces 174" that are substantially cylindrical and extend from a top surface 164" to near a bottom surface 169" of the insert 14". In other words, the insert 14" does not include the tapered surfaces 163 of the insert 14. The arm surfaces 174" are fully and slidingly received by the receiver surfaces 84 as well as the other receiver 10 inner arm surfaces and thus the insert 14" cannot be wedged into the receiver 10 to independently lock the polyaxial mechanism of the assembly 1. In all other respects, the insert 14" functions the same as the insert 14.

With reference to FIGS. 1 and 34-36, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys, non-metals and deformable and less compressible plastics, including, but not limited to rods made of elastomeric, polyetheretherketone (PEEK) and other types of materials, such as polycarbonate urethanes (PCU) and polyethelenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 34-36, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes a an outer helically wound guide and advancement structure 182 in the form of a flange that operably joins with the guide and advancement structure 72 disposed on the arms 62 of the receiver 10. The flange form utilized in accordance with the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 10 that may more advantageously engage longitudinal connecting member components. The illustrated closure structure 18 also includes a top surface 184 with an internal drive 186 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 186 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 188 of the closure is planar and further includes a point 189 and a rim 190 for engagement and penetration into the surface 22 of the rod 21 in certain embodiments of the invention. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62.

An alternative closure top 18' for use with a deformable rod 21', such as a PEEK rod, is shown in FIG. 37. The top 18' is identical to the top 18 with the exception that a point 189' is located on a domed surface 190' in lieu of the planar bottom with point and rim of the closure top 18.

Preferably, the receiver 10, the retainer 12 and the compression insert 14 are assembled at a factory setting that includes tooling for holding and alignment of the component pieces and pinching or compressing of the retainer 12 spring tabs 118 and rotating and otherwise manipulating the insert 14 arms, as well as crimping a portion of the receiver 10 toward the insert 14. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost and improving logistics and distribution.

Figure 22:
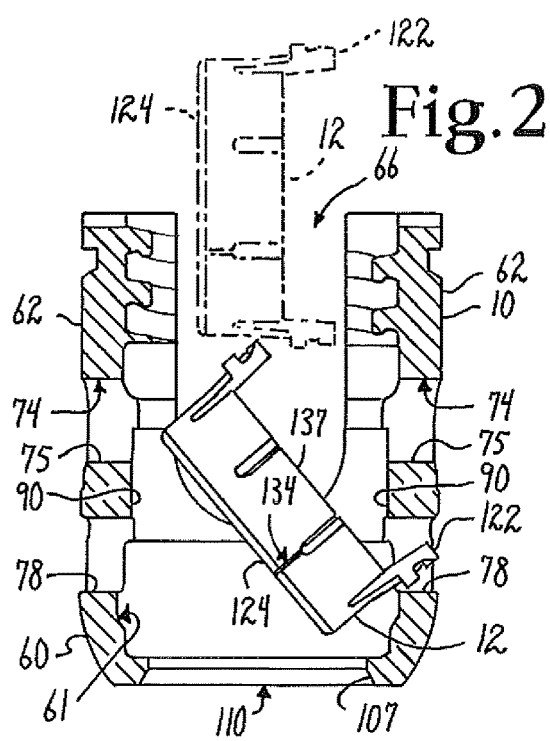
FIG. 22 is an enlarged front elevational view of the retainer and receiver of FIG. 1 with portions of the receiver broken away (as illustrated in FIG. 27) to show the detail thereof, the retainer being shown downloaded into the receiver (in phantom) to a partially inserted stage of assembly.

Pre-assembly of the receiver 10, retainer 12 and compression insert 14 is shown in FIGS. 22-28. With particular reference to FIG. 22, first the retainer 12 is inserted into the upper receiver opening 66, leading with one of the spring tabs 118 with both of the spring tab top surfaces 122 facing one arm 62 and the retainer bottom surface 124 facing the opposing arm 62 (shown in phantom). The retainer 12 is then lowered in such sideways manner into the channel 64 and partially into the receiver cavity 61, followed by tilting the retainer 212 such that the top surface 122 and thereafter the outer tab or wing 140 of the leading spring tab 118 is moved into a nearby receiver arm through bore 78. With reference to FIG. 23, the retainer 12 is then further tilted or turned and manipulated within the receiver to a position within the cavity until the retainer 12 bottom surface 124 is directed toward the receiver cavity 61 and the spring tab upper surfaces 122 are facing upwardly toward the receiver channel opening 66. To accomplish such tilting and turning of the retainer 12, the spring tab arm 118 located within the receiver bore 78 is manipulated downwardly and then upwardly within the bore 78 and finally shifted out of the bore 78 when the opposed spring tab arm 118 outer tab or wing 140 moves past and clears the cylindrical surface 84 of the receiver 10. Once the retainer bottom surface 124 seats on the receiver surface 104, both of the spring tab wings 140 are partially located in opposed receiver bores 78.

Figure 24:
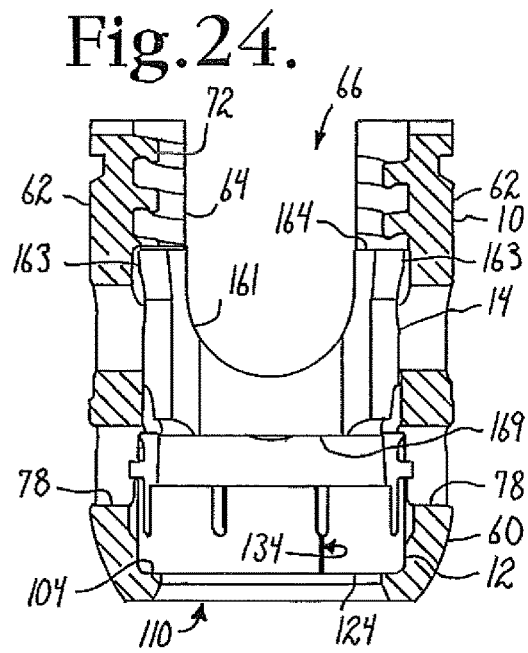
FIG. 24 is a front elevational view with portions broken away, similar to FIG. 23, showing the insert rotated into a position in alignment with the receiver.
Figure 25:
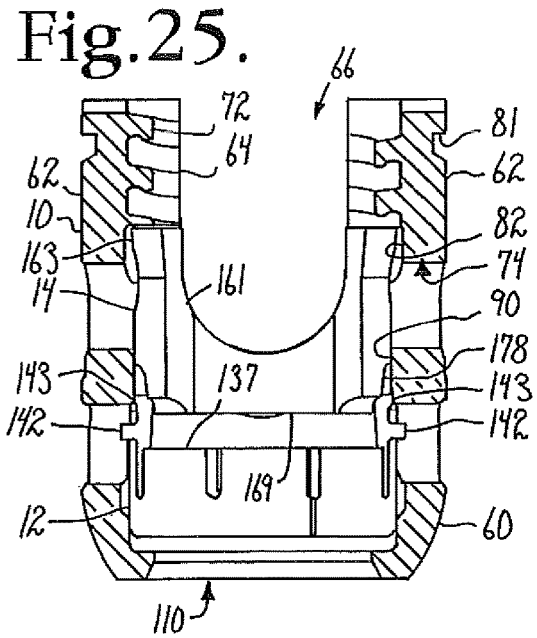
FIG. 25 is a front elevational view with portions broken away, similar to FIG. 24 showing arms or upwardly extending spring tabs of the retainer being pinched (with a tool not shown) towards one another and the retainer partially moved upwardly within the receiver.

With reference to FIGS. 23 and 24, the compression insert 14 is then downloaded into the receiver 10 through the upper opening 66 with the bottom surface 169 facing the receiver arm top surfaces 73 and the insert arms 157 located between the opposed receiver arms 62. The insert 14 is then lowered toward the channel seat 68 until the insert 14 arm upper surfaces 164 are adjacent the run-out area below the guide and advancement structure 72 defined in part by the cylindrical surface 82. Thereafter, the insert 14 is rotated in a clockwise or counter-clockwise manner about the receiver axis B until the upper arm surfaces 164 are directly below the guide and advancement structure 72 as illustrated in FIG. 24 with the U-shaped channel 161 of the insert 14 aligned with the U-shaped channel 64 of the receiver 10. In some embodiments, the insert arms 157 may need to be compressed slightly during rotation to clear inner surfaces of the receiver arms 62. As shown in FIGS. 24 and 25, the outer lower cylindrical surface 174 of the insert 14 is received within the cylindrical surface 90 of the receiver.

Figure 26:
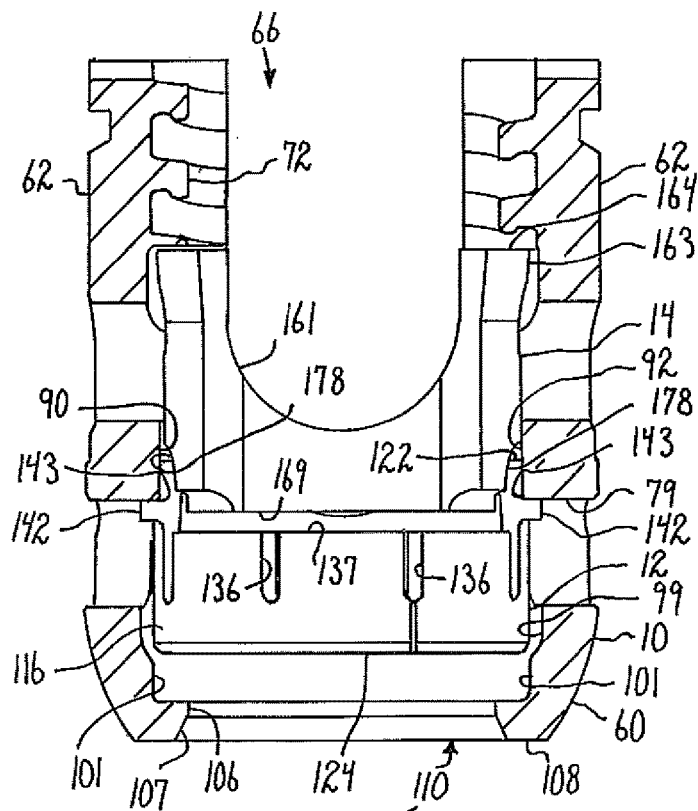
FIG. 26 is a front elevational view similar to FIG. 25 showing the retainer arms placed in a desired upward position within the receiver and the pinching tool removed so that the retainer pushes outwardly against the receiver and is held against the receiver during shipping.
Figure 27:
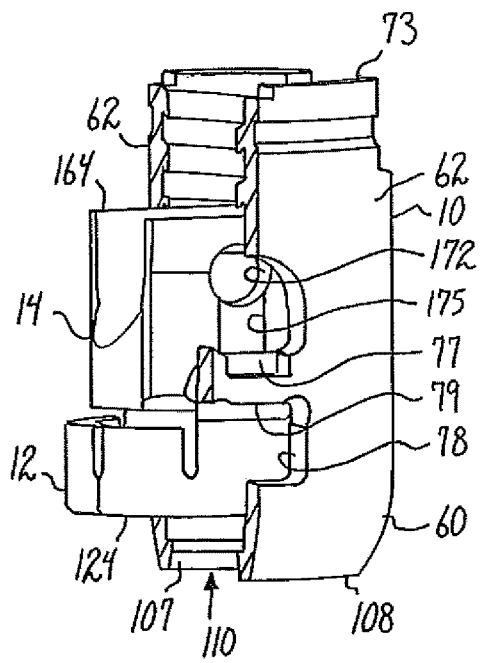
FIG. 27 is a reduced perspective view with portions broken away of the assembly as shown in FIG. 26.
Figure 28:
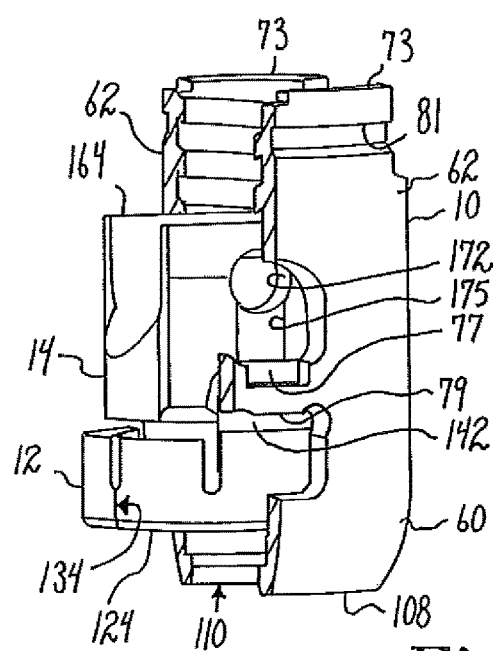
FIG. 28 is a perspective view with portions broken away, similar to FIG. 27, showing a portion of the receiver crimped against the insert.

With further reference to FIGS. 24 and 25, a tool (not shown) is then used to grip the retainer spring tab arms 118 at outer surfaces thereof and squeeze or press the tabs 118 toward one another while moving the retainer 12 in an upward direction away from the surface 104. With reference to FIG. 26, when the spring tab wing surface projections 142 abut against the surface 79, the tool (not shown) is released and a portion or portions 143 of each spring tab 118 spring out to engage the surface portion 92 formed in the receiver cylindrical surface 90. With reference to FIGS. 26-28, the retainer 12 is now in a desired position for shipping as an assembly along with the separate shank 4. The insert 14 recessed areas 178 are now located adjacent to the retainer spring tab top surfaces 122.

With reference to FIGS. 27 and 28, prior to shipping the receiver thin walls 77 are then crimped inwardly toward the axis B by inserting a tool (not shown) through the receiver apertures 74, the tool pressing the walls 77 until the wall surface 87 engages the insert 14 at the shallow central grooves 175 formed on the outer surface 174 of each of the insert arms 157. The crimping of the wall surface 93 into the groove 175 keeps the insert 14 U-shaped channel 161 aligned with the receiver U-shaped channel 64 and also helps retain the insert 14 at the upward location shown in FIG. 26 with the insert arm top surfaces 164 adjacent the guide and advancement structure 72 until the insert 14 is pushed downwardly toward the receiver base 60 after assembly with the shank 4. Thus, the crimping of the receiver walls 77 helps hold the insert 14 in position and prohibits rotation of the insert 14 about the receiver axis B but allows for limited axial movement of the insert 14 with respect to the receiver 10 along the axis B when some force is exerted to slide the crimped surface 93 up or down along the groove 175. The insert 14 is fully captured within the receiver 10 by the guide and advancement structure 72 prohibiting movement of the insert 14 up and out through the receiver opening 66 as well as by retainer 12 located below the insert.

Typically, the receiver and retainer combination are shipped or otherwise provided to the end user with the spring tab outer wings 140 wedged against the receiver as shown in FIG. 26. The receiver 10, retainer 12 and insert 14 combination is now pre-assembled and ready for assembly with the shank 4 either at the factory, by surgery staff prior to implantation, or directly upon an implanted shank 4 as will be described herein.

Figure 29:
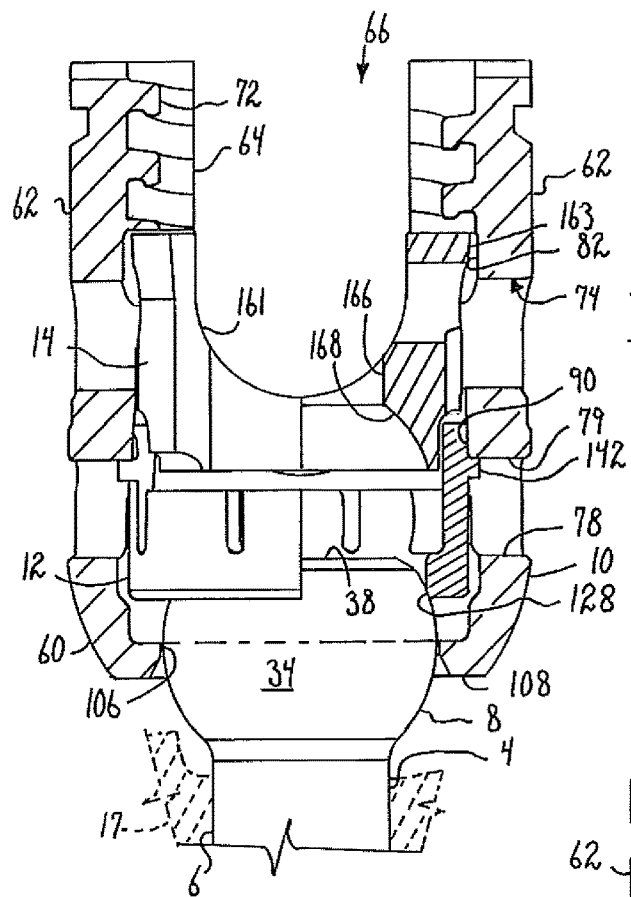
FIG. 29 is an enlarged front elevational view with portions broken away, similar to FIG. 26, also including the crimping of FIG. 28 and further showing an enlarged and partial shank of FIG. 1 in a first stage of assembly with the retainer, a hemisphere of the shank head and a vertebra portion are both shown in phantom.

As illustrated in FIG. 29, the bone screw shank 4 or an entire assembly 1 made up of the assembled shank 4, receiver 10, retainer 12 and compression insert 14, is screwed into a bone, such as the vertebra 17 (shown in phantom), by rotation of the shank 4 using a suitable driving tool (not shown) that operably drives and rotates the shank body 6 by engagement thereof at the internal drive 46. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires and attachable tower tools mating with the receiver. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

Figure 30:
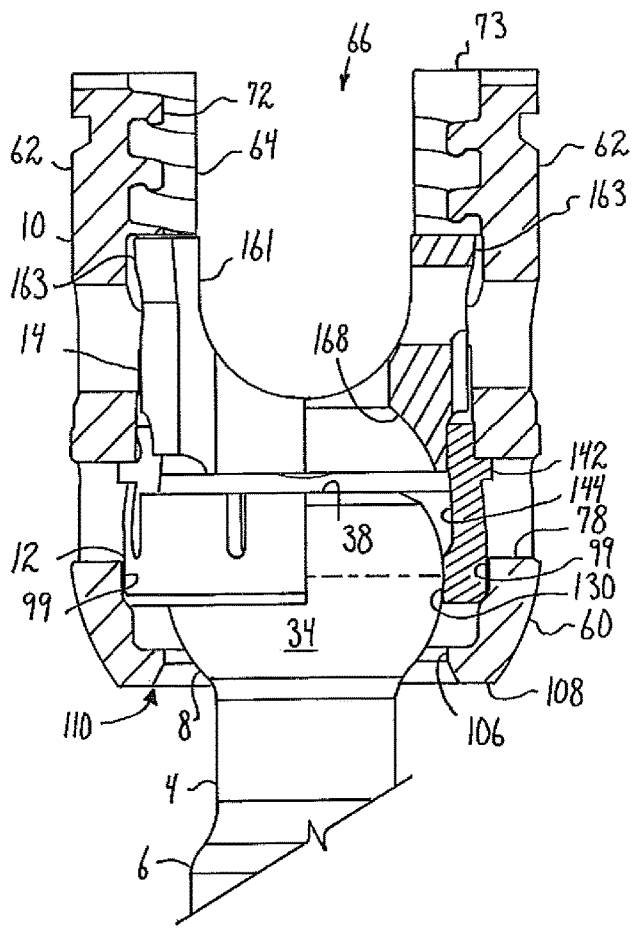
FIG. 30 is a partial front elevational view with portions broken away, similar to FIG. 29, showing the retainer lower portion in an expanded state about a mid-portion of the shank head, the head hemisphere shown in phantom.
Figure 31:
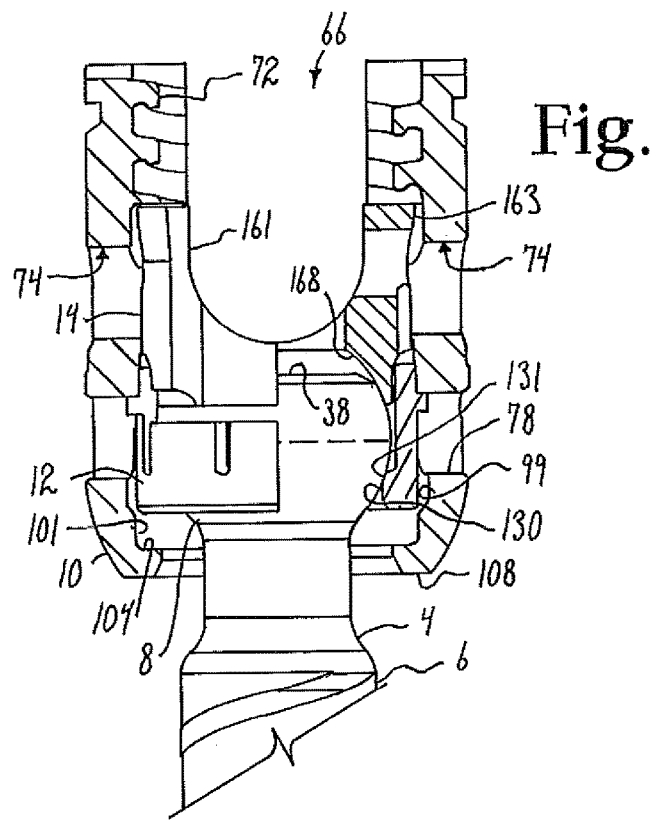
FIG. 31 is a reduced partial front elevational view with portions broken away, similar to FIG. 30, the shank upper portion or head in frictional engagement with an upper portion of the retainer.
Figure 32:
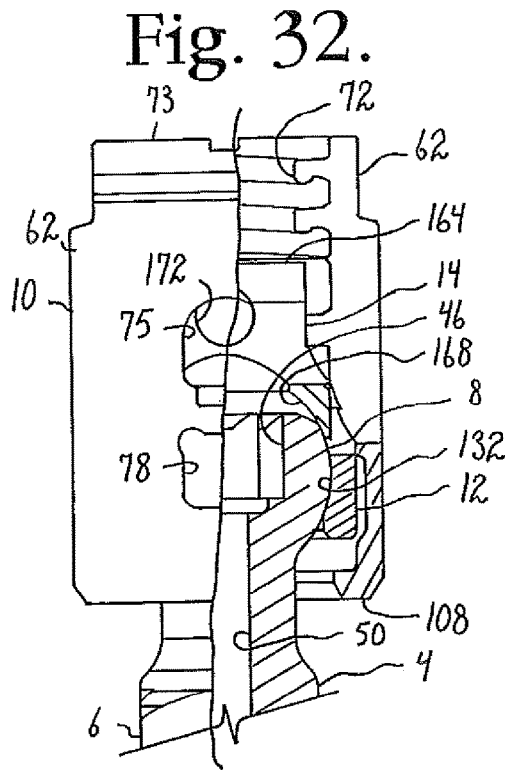
FIG. 32 is a partial side elevational view with portions broken away of the assembly in a stage as shown in FIG. 31.

With further reference to FIG. 29, the pre-assembled receiver, insert and retainer are placed above the shank upper portion 8 until the shank upper portion is received within the opening 110. With particular reference to FIGS. 30 and 31, as the shank upper portion 8 is moved into the interior 61 of the receiver base, the shank upper portion 8 presses upwardly against the retainer 12 in the recess partially defined by the cylindrical surface 99. As the portion 8 continues to move upwardly toward the channel 64, the surface 34 forces outward movement of the retainer 12 towards the cylindrical surface 99 defining the receiver expansion recess or chamber. The retainer 12 begins to return to its neutral state as the center of the sphere (shown in dotted lines) passes beyond the center of the retainer expansion recess. At this time also, the spherical surface 34 moves into engagement with the surfaces 132 of the retainer flex tabs or panels 117, the panels 117 expanding slightly outwardly to receive the surface 34. With reference to FIG. 32, the spherical surface 34 then enters into full frictional engagement with the panel inner surfaces 132. At this time, the retainer 12 panels and the surface 34 are in a fairly tight friction fit, the surface 34 being pivotable with respect to the retainer 12 with some force. Thus, a tight, non-floppy ball and socket joint is now created between the retainer 12 and the shank upper portion 8.

Figure 33:
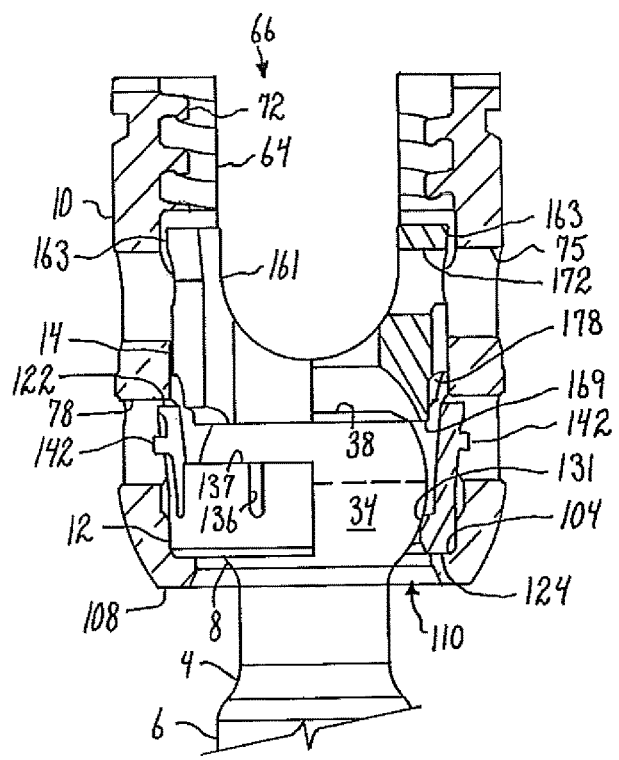
FIG. 33 is a partial front elevational view with portions broken away, similar to FIG. 31, the shank upper portion with attached retainer being shown pulled down into a seated position within the lower receiver cavity.

With reference to FIG. 33, the receiver is then pulled upwardly or the shank 4 and attached retainer 12 are then moved downwardly into a desired position with the retainer seated on the surface 104. Again, this may be accomplished by either an upward pull on the receiver 10 or, in some cases, by driving the shank 4 further into the vertebra 17. The insert 14 may be pressed downwardly by a tool or by a rod and closure top as shown in FIG. 34. Also, in some embodiments, when the receiver 10 is pre-assembled with the shank 4, the entire assembly 1 may be implanted at this time by inserting the driving tool (not shown) into the receiver and the shank drive 46 and rotating and driving the shank 4 into a desired location of the vertebra 17. Also, when the retainer 12 moves down into the locking chamber, the spring tabs are deployed out into the openings 78 and the shank and retainer cannot move back up again within the receiver.

Also with reference to FIGS. 33 and 34, prior to assembly with the rod 21 and the closure top 18, the compression insert 14 frusto-conical surface 163 is near the surface 84. The insert 14 is prohibited from moving any further downwardly at the beginning of the surface 84 unless forced downwardly by a locking tool or by the closure top pressing downwardly on the rod that in turn presses downwardly on the insert 14 as shown in FIG. 34. With further reference to FIG. 33 and also to FIG. 35, at this time, the receiver 10 may be articulated to a desired angular position with respect to the shank 4, such as that shown in FIG. 35, that will be held, but not locked, by the frictional engagement between the retainer 12 and the shank upper portion 8.

The rod 21 is eventually positioned in an open or percutaneous manner in cooperation with the at least two bone screw assemblies 1. The closure structure 18 is then inserted into and advanced between the arms 62 of each of the receivers 10. The closure structure 18 is rotated, using a tool engaged with the inner drive 186 until a selected pressure is reached at which point the rod 21 engages the U-shaped seating surface 162 of the compression insert 14, further pressing the insert spherical surface 168 (or stepped shank gripping surfaces 170 of the insert 14') against the shank spherical surface 34, (the edges of the stepped surfaces 170 penetrating into the spherical surface 34), pressing the shank upper portion 8 into locked frictional engagement with the retainer 12. Specifically, as the closure structure 18 rotates and moves downwardly into the respective receiver 10, the point 189 and rim 190 engage and penetrate the rod surface 22, the closure structure 18 pressing downwardly against and biasing the rod 21 into compressive engagement with the insert 14 that urges the shank upper portion 8 toward the retainer 12 and into locking engagement therewith, the retainer 12 frictionally abutting the surface 104 and expanding outwardly against the cylindrical surface 101. For example, about 80 to about 120 inch pounds of torque on the closure top may be applied for fixing the bone screw shank 6 with respect to the receiver 10.

Also, as the closure structure 18 and the rod 21 press the insert 14 downwardly toward the base of the receiver 10, the insert frusto-conical surface 163 is forced into the receiver cylindrical surface 84, wedging the insert 14 into fixed frictional engagement with the receiver surface 84. With reference to FIG. 36, at this time, the closure top 18 may be loosened or removed and/or the rod 21 may be adjusted and/or removed and the frictional engagement between the insert 14 and the receiver 10 at the receiver surface 84 will remain locked in place, advantageously maintaining a locked angular position of the shank 4 with respect to the receiver 10. If the user wishes to release the insert 14 from the receiver 10 and unlock the polyaxial mechanism, a tool (not shown) may be used that includes extensions or prongs that are received by and through the opposed through bores 75 of the receiver 10 and received into the through bores 172 of the insert 14. Such tool is then pulled upwardly in a direction along the axis B away from the receiver base 60, thereby pulling the insert slightly upwardly and away from the receiver base 60 and releasing the frusto-conical surface 163 from the cylindrical surface 84. Alternatively, if both the closure top 18 and the rod 21 are already removed from the receiver 10, another manipulation tool (not shown) may be used that is inserted into the receiver at the opening 66 and into the insert channel 161, with prongs or extensions thereof extending outwardly into the insert through bores 172; a piston-like portion of the tool thereafter pushing directly on the shank upper portion 8, thereby pulling the insert 14 surface 163 away from the receiver surface 84 and thus releasing the polyaxial mechanism. At such time, the shank 4 may be articulated with respect to the receiver 10, and the desired friction fit returns between the retainer 12 and the shank surface 34, so that an adjustable, but non-floppy relationship still exists between the shank 4 and the receiver 10. If further disassembly if the assembly 1 is desired, such is accomplished in reverse order to the procedure described previously herein for assembly.

With reference to FIG. 37, an alternative assembly 1' is shown in which the rod 21 and closure top 18 of the assembly 1 of FIG. 36 are replaced with a deformable rod 18' and alternative closure top 18'. Because of the lock between the insert 14 and the receiver 10, any loosening of the rod 21' from the receiver 10 that may occur due to rod deformation does not compromise the locked polyaxial mechanism formed by the wedged in insert 14, the shank upper portion 8, the retainer 12 and the receiver 10.

It is to be understood that while certain forms of the present invention have been illustrated and described herein, it is not to be limited to the specific forms or arrangement of parts described and shown.

What is claimed is:

1. A pivotal bone anchor assembly comprising:
 a bone anchor having a capture portion with a partially spherical outer surface and an integral anchor portion opposite the capture portion configured for fixation to a bone;
 a longitudinal connecting member having a circular cross-section; and
 a receiver assembly in a pre-assembled configuration configured to receive the capture portion of the bone anchor, the receiver assembly in the pre-assembled configuration including:
  a receiver comprising a base defining a lower portion of a central bore centered about a vertical centerline axis and communicating with a bottom surface of the receiver through a bottom opening, and a pair of upright arms integrally formed with and extending upwardly from the base to define an open channel extending between a front side and a back side of the receiver and configured to downwardly receive the longitudinal connecting member, the central bore extending upwardly through the open channel to tops of the upright arms and flanked on both sides by opposed substantially-planar surfaces extending between the central bore and the front side and the back side of the receiver and extending parallel with the respect to the vertical centerline axis, the central bore configured to receive the capture portion of the bone anchor through the bottom opening and having a narrower engagement portion adjacent the bottom opening, a wider expansion portion above the narrower engagement portion, and inwardly-facing interference wedging surfaces above the wider expansion portion extending to the opposed substantially-planar surfaces flanking the central bore;
  a retainer disposed within the wider expansion portion of the central bore and having a concave interior surface operable to grip the at least partially spherical outer surface of the capture portion of the bone anchor, the retainer configured to widen within the wider expansion portion so as to receive the capture portion within the retainer when the capture portion is uploaded through the bottom opening, and then to close around and secure the capture portion within the central bore while providing for pivotal motion of the bone anchor relative to the receiver; and
  a pressure insert positioned within the central bore above the retainer disposed within the wider expansion portion, the pressure insert having an upwardly-open rod seat configured to downwardly receive the longitudinal connecting member through the open channel, and a recess below the rod seat configured to receive an upper portion of the retainer prior to the capture portion of the bone anchor being uploaded through the bottom opening,
 wherein after the capture portion of the bone anchor is uploaded through the bottom opening and secured within the retainer, and prior to the installation of the longitudinal connecting member,
  the pressure insert with an empty rod seat is downwardly deployable within the central bore of the receiver by tooling until an outer surface of the pressure insert comes into forced interference wedged engagement with the interference wedging surfaces of the central bore so as to inhibit the pressure insert from moving back up within the receiver, and the retainer together with the capture portion of the bone anchor secured therein are downwardly displaceable within the central bore with outer surfaces of the retainer entering into engagement with the narrower engagement portion of the central bore to impede repeated widening of the retainer, and wherein the empty rod seat of the pressure insert and the open channel of the receiver are configured to downwardly receive at least a portion of the longitudinal connecting member when the pressure insert, in the downwardly deployed position, is in the forced interference wedged engagement with the interference wedging surfaces.

2. The pivotal bone anchor assembly of claim 1, wherein the upwardly-open rod seat of the pressure insert further comprises a curvate surface with at least one seat radius that is substantially equal to a radius of the circular cross-section of the longitudinal connecting member.

3. The pivotal bone anchor assembly of claim 1, wherein the retainer includes at least one slot extending from a top surface to a bottom surface of the retainer.

4. The pivotal bone anchor assembly of claim 1, wherein the upper portion of the retainer extends above a top surface of the capture portion of the bone anchor when the capture portion is captured within the retainer.

5. The pivotal bone anchor assembly of claim 1, wherein the retainer is configured to frictionally engage the capture portion of the bone anchor when the capture portion is received within the retainer so as to provide an unlocked but non-floppy friction fit positioning of the bone anchor relative to the receiver prior to a final locking of the pivotal bone anchor assembly.

6. The pivotal bone anchor assembly of claim 1, wherein the retainer is non-pivotal with respect to the receiver after the capture portion of the bone anchor is secured therein.

7. The pivotal bone anchor assembly of claim 1, wherein the retainer is in a non-contracted state when in a downwardly deployed and locked position within the narrower engagement portion of the central bore.

8. The pivotal bone anchor assembly of claim 1, wherein the pressure insert is configured to engage the capture portion of the bone anchor.

9. The pivotal bone anchor assembly of claim 1,
wherein the pressure insert further includes a downwardly-facing surface configured for engagement by the tooling, and wherein the pressure insert is configured to be released from the forced interference wedged engagement and moved back up within the central bore by the tooling in engagement with the downwardly-facing surface.

10. The pivotal bone anchor assembly of claim 9, wherein the downwardly-facing surface of the pressure insert is engageable by the tooling through the central bore of the receiver.

11. The pivotal bone anchor assembly of claim 1, wherein the inwardly-facing interference wedging surfaces of the central bore are cylindrical and the outer surface of the pressure insert is non-cylindrical and configured for becoming wedged against the cylindrical inwardly-facing interference wedging surfaces.

12. The pivotal bone anchor assembly of claim 1, wherein the inwardly-facing interference wedging surfaces of the central bore are non-cylindrical and the outer surface of the pressure insert is cylindrical and configured for becoming wedged against the non-cylindrical inwardly-facing interference wedging surfaces.

13. The pivotal bone anchor assembly of claim 1 and further comprising a closure,
wherein the closure has a receiver-mating structure formed into an outer sidewall surface of the closure that is complementary with a closure-mating structure formed into an upper portion of the central bore of the receiver adjacent the tops of the upright arms, and wherein after the longitudinal connecting member is positioned within the open channel, the receiver-mating structure is configured to engage with the closure-mating structure so as to apply a downward pressure to a top of the longitudinal connecting member to secure the longitudinal connecting member to the bone.

14. The pivotal bone anchor assembly of claim 13, wherein the receiver-mating structure of the closure and the closure-mating structure of the receiver each further comprise complementary helical threads formed on the outer sidewall surface of the closure and on inner surfaces of the central bore adjacent the tops of the upright arms, respectively.

15. The pivotal bone anchor assembly of claim 13, wherein the pressure insert is further configured for downward deployment within the central bore and into the forced interference wedged engagement with the inwardly-facing interference wedging surfaces of the central bore by the downward pressure applied to the top of the longitudinal connecting member during the engagement between the receiver-mating structure with the closure-mating structure.

16. A pivotal bone anchor assembly comprising:
a bone anchor having an capture portion with an at least partially spherical outer surface and an integral anchor portion opposite the capture portion configured for fixation to a bone;

a longitudinal connecting member having a circular cross-section;

a receiver comprising a base defining a lower portion of a central bore centered about a vertical centerline axis and communicating with a bottom surface of the receiver through a bottom opening, and a pair of upright arms extending upwardly from the base to define an open channel extending between a front side and a back side of the receiver and configured to downwardly receive the longitudinal connecting member, the central bore extending upwardly through the open channel to tops of the upright arms and flanked on both sides by opposed inner planar surfaces extending between the central bore and the front side and the back side of the receiver and extending parallel with the respect to the vertical centerline axis, the central bore configured to receive the capture portion of the bone anchor through the bottom opening and having a narrower engagement portion adjacent the bottom opening, a wider expansion portion above the narrower engagement portion, and inwardly-facing interference wedging surfaces above the wider expansion portion extending to each of the opposed inner planar surfaces flanking the center bore;

a retainer having a concave interior surface operable to grip the at least partially spherical outer surface of the capture portion of the bone anchor, the retainer configured for initial positioning within the wider expansion portion of the central bore and to widen so as to receive the capture portion when the capture portion is uploaded through the bottom opening, and then to close around and secure the capture portion within the central bore while providing for pivotal motion of the bone anchor relative to the receiver; and a pressure insert configured for initial positioning within the central bore above and in a partially side-to-side overlapping relationship with the retainer that is disposed within the wider expansion portion prior to the capture portion of the bone anchor being captured by the retainer, the pressure insert having an upwardly-open rod seat configured to downwardly receive the longitudinal connecting member, wherein after the capture portion of the bone anchor is uploaded through the bottom opening and secured within the retainer, and prior to the installation of the longitudinal connecting member, the retainer and the pressure insert with an empty rod seat are configured to be downwardly deployed within the central bore by tooling until an outer surface of the retainer engages an interior surface of the narrower engagement portion to impede repeat widening of the retainer and an outer surface of the pressure insert comes into forced interference wedged engagement with the interference wedging surfaces of the central bore to inhibit the pressure insert from moving back up within the receiver, and wherein the empty rod seat of the pressure insert and open channel of the receiver are configured to downwardly receive the longitudinal connecting member when the pressure insert, in the downwardly deployed position, is in the forced interference wedged engagement with the interference wedging surfaces.

17. The pivotal bone anchor assembly of claim 16, wherein the upwardly-open rod seat of the pressure insert further comprises a curvate surface with at least one seat radius that is equal to or about a radius of the circular cross-section of the longitudinal connecting member.

18. The pivotal bone anchor assembly of claim 16, wherein the retainer includes at least one through-and-through slot extending through the interior surface and an exterior surface and a top and a bottom thereof.

19. The pivotal bone anchor assembly of claim 16, wherein an upper portion of the retainer extends above a top surface of the capture portion of the bone anchor after the capture portion is received and secured therein.

20. The pivotal bone anchor assembly of claim 16, wherein the retainer is non-pivotal with respect to the receiver after the capture portion of the bone anchor is received and secured therein.

21. The pivotal bone anchor assembly of claim 16, wherein the retainer is a resilient expandable structure.

22. The pivotal bone anchor assembly of claim 16, wherein the outer surface of the retainer is at least partially tapered.

23. The pivotal bone anchor assembly of claim 16, wherein the pressure insert is configured to engage the capture portion of the bone anchor.

24. The pivotal bone anchor assembly of claim 16,
wherein the pressure insert further includes a downwardly-facing surface configured for engagement by the tooling, and
wherein the pressure insert is configured to be released from the forced interference wedged engagement and moved back up within the central bore by the tooling in engagement with the downwardly-facing surface.

25. The pivotal bone anchor assembly of claim 24, wherein the downwardly-facing surface of the pressure insert is engageable by the tooling through the central bore of the receiver.

26. The pivotal bone anchor assembly of claim 16 and further comprising a closure,
wherein the closure has a receiver-mating structure formed into an outer sidewall surface of the closure that is complementary with a closure-mating structure formed into an upper portion of the central bore of the receiver adjacent the tops of the upright arms, and
wherein after the longitudinal connecting member is positioned within the open channel, the receiver-mating structure is configured to engage with the closure-mating structure so as to apply a downward pressure to a top of the longitudinal connecting member to secure the longitudinal connecting member to the bone.

* * * * *